(12) United States Patent
Akita et al.

(10) Patent No.: US 7,893,293 B2
(45) Date of Patent: Feb. 22, 2011

(54) CHEMICALLY AMPLIFIED POSITIVE RESIST COMPOSITION

(75) Inventors: Makoto Akita, Hsin-Chu (TW); Isao Yoshida, Ikeda (JP); Kazuhiko Hashimoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 308 days.

(21) Appl. No.: 12/143,268

(22) Filed: Jun. 20, 2008

(65) Prior Publication Data

US 2009/0004600 A1 Jan. 1, 2009

(30) Foreign Application Priority Data

Jun. 22, 2007 (JP) ............................... 2007-164929

(51) Int. Cl.
C07C 69/753 (2006.01)
C07C 43/21 (2006.01)
C07C 43/215 (2006.01)
C08F 12/32 (2006.01)
G03F 7/039 (2006.01)

(52) U.S. Cl. ............................. 560/8; 560/5; 568/592; 568/593; 568/609; 568/632; 526/284; 526/313; 526/320; 526/326; 526/333; 526/334; 430/905

(58) Field of Classification Search ....................... None
See application file for complete search history.

(56) References Cited

U.S. PATENT DOCUMENTS

2003/0013038 A1 1/2003 Ichimura et al.
2003/0207200 A1* 11/2003 Barclay et al. ........... 430/270.1
2005/0042540 A1 2/2005 Okubo et al.

FOREIGN PATENT DOCUMENTS

JP 2002-341523 * 11/2002
JP 2006-330401 A 12/2006

OTHER PUBLICATIONS

JPO English abstract for JP2002-341523.*
Machine-assited English translation of JP2002-341523 provided by JPO.*

* cited by examiner

*Primary Examiner*—Sin J. Lee
(74) *Attorney, Agent, or Firm*—Birch, Stewart, Kolasch & Birch, LLP

(57) ABSTRACT

A chemically amplified positive resist composition comprising (A) a resin which comprises (i) a polymerization unit represented by the formula (I):

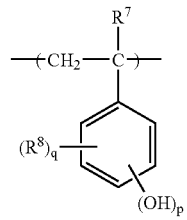

(I)

wherein $R^7$ represents a hydrogen atom etc., $R^8$ represents a C1-C4 alkyl group, p represents an integer of 1 to 3, and q represents an integer of 0 to 2,
(ii) at least one polymerization unit selected from a group consisting of a polymerization unit represented by the formula (II):

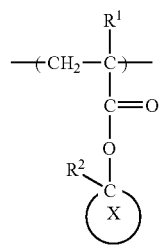

(II)

wherein $R^1$ represents a hydrogen atom etc., $R^2$ represents a C1-C8 alkyl group and ring X represents an alicyclic hydrocarbon group, and a polymerization unit represented by the formula (IV):

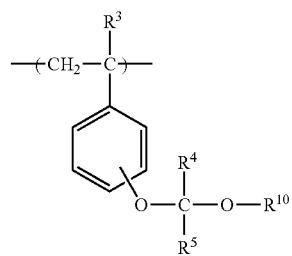

(IV)

wherein $R^3$ represents a hydrogen atom etc., $R^4$ and $R^5$ independently represents a hydrogen atom etc., $R^{10}$ represents a C1-C6 alkyl group etc., and
(iii) a polymerization unit represented by the formula (III):

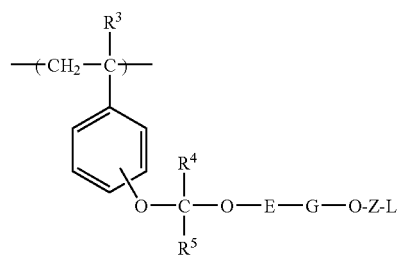

(III)

wherein $R^3$, $R^4$ and $R^5$ are the same as defined above, E represents a divalent hydrocarbon group, G represents a single bond etc., Z represents a carbonyl group etc. and L represents an anthryl group etc., and
(B) at least one acid generator.

2 Claims, No Drawings

CHEMICALLY AMPLIFIED POSITIVE RESIST COMPOSITION

This nonprovisional application claims priority under 35 U.S.C. §119(a) on Patent Application No. 2007-164929 filed in JAPAN on Jun. 22, 2007, the entire contents of which are hereby incorporated by reference.

FIELD OF THE INVENTION

The present invention relates to a chemically amplified positive resist composition.

BACKGROUND OF THE INVENTION

A chemically amplified positive resist composition is used for semiconductor microfabrication employing a lithography process using i-rays, KrF, ArF and electron beam; forming a bump or a thick film resist pattern in the production of semiconductor devices; forming a wiring pattern or a thick film resist laminated body in the production of circuit board; and the like.

It is expected for the chemically amplified resist composition to give patterns having high resolution and good pattern profile.

US 2005/0042540 A1 discloses a chemically amplified positive resist composition comprising a resin which comprises a polymerization unit derived from hydroxystyrene and a polymerization unit derived from a (meth)acrylate ester, and an acid generator.

SUMMARY OF THE INVENTION

The present invention relates to the followings:

<1> A chemically amplified positive resist composition comprising (A) a resin which comprises (i) a polymerization unit represented by the formula (I):

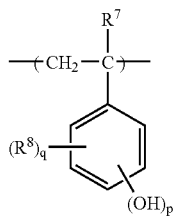

(I)

wherein $R^7$ represents a hydrogen atom or a C1-C4 alkyl group, $R^8$ represents a C1-C4 alkyl group, p represents an integer of 1 to 3, and q represents an integer of 0 to 2, and when q is 1 or 2, $R^8$ may be the same or different, (ii) at least one polymerization unit selected from a group consisting of a polymerization unit represented by the formula (II):

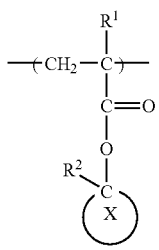

(II)

wherein $R^1$ represents a hydrogen atom or a C1-C4 alkyl group, $R^2$ represents a C1-C8 alkyl group and ring X represents an alicyclic hydrocarbon group, and a polymerization unit represented by the formula (IV):

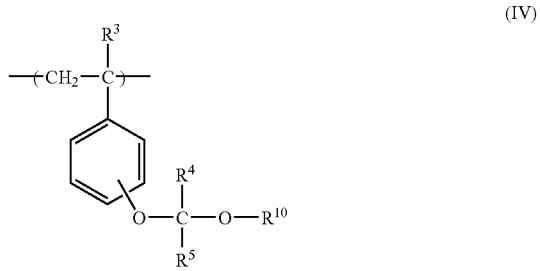

(IV)

wherein $R^3$ represents a hydrogen atom or a C1-C4 alkyl group, $R^4$ and $R^5$ independently represents a hydrogen atom or a C1-C4 alkyl group, $R^{10}$ represents a C1-C6 alkyl group or a C5-C7 cycloalkyl group, and $R^4$ and $R^{10}$ or $R^5$ and $R^{10}$ may be bonded to form a trimethylene group or a tetramethylene group, and (iii) a polymerization unit represented by the formula (III):

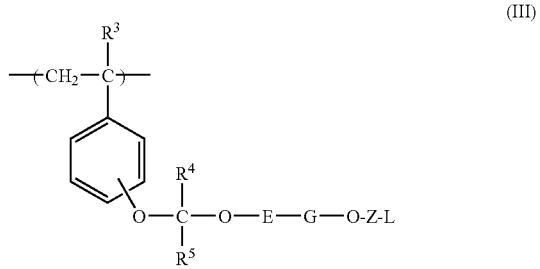

(III)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, Z represents a single bond, an alkylene group or a carbonyl group and L represents a phenyl group which is substituted with two C1-C6 alkoxy groups at 3- and 4-position and may be further substituted with at least one C1-C6 alkoxy group, a naphthyl group which may be substituted with at least one C1-C6 alkoxy group, an anthryl group which may be substituted with at least one C1-C6 alkoxy group, or a phenanthryl group which may be substituted with at least one C1-C6 alkoxy group, and (B) at least one acid generator;

<2> The chemically amplified positive resist composition according to <1>, wherein the polymerization unit represented by the formula (II) is a polymerization unit represented by the formula (IIa):

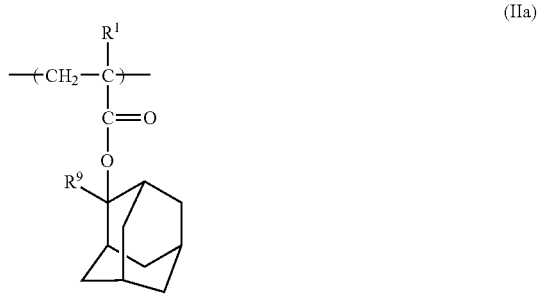

(IIa)

wherein $R^1$ represents a hydrogen atom or a methyl group and $R^9$ represents a C1-C8 alkyl group;

<3> The chemically amplified positive resist composition according to <1> or <2>, wherein p is 1 and q is 0 in the formula (I);

<4> The chemically amplified positive resist composition according to <1>, <2> or <3>, wherein at least one acid generator comprises diazomethane compound having a sulfonyl group;

<5> The chemically amplified positive resist composition according to any one of <1> to <4>, wherein the content of the polymerization unit represented by the formula (III) are in the range of 0.1 to 50% by mole based on all polymerization units of the resin;

<6> The chemically amplified positive resist composition according to any one of <1> to <5>, wherein the chemically amplified positive resist composition further comprises a basic compound;

<7> A chemically amplified positive resist composition comprising (A1) a resin which comprises (iv) a polymerization unit represented by the formula (I):

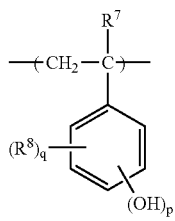

(I)

wherein $R^7$ represents a hydrogen atom or a C1-C4 alkyl group, $R^8$ represents a C1-C4 alkyl group, p represents an integer of 1 to 3, and q represents an integer of 0 to 2, and when q is 1 or 2, $R^8$s may be the same or different, and (v) at least one polymerization unit selected from a group consisting of a polymerization unit represented by the formula (II):

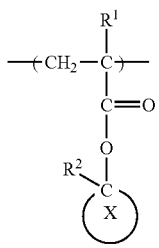

(II)

wherein $R^1$ represents a hydrogen atom or a C1-C4 alkyl group, $R^2$ represents a C1-C8 alkyl group and ring X represents an alicyclic hydrocarbon group, and a polymerization unit represented by the formula (IV):

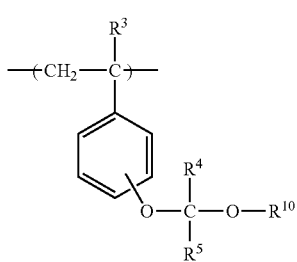

(IV)

wherein $R^3$ represents a hydrogen atom or a C1-C4 alkyl group, $R^4$ and $R^5$ independently represents a hydrogen atom or a C1-C4 alkyl group, $R^{10}$ represents a C1-C6 alkyl group or a C5-C7 cycloalkyl group, and $R^4$ and $R^{10}$ or $R^5$ and $R^{10}$ may be bonded to form a trimethylene group or a tetramethylene group, (A2) a resin which comprises (Vi) the polymerization unit represented by the formula (I) and (vii) a polymerization unit represented by the formula (III).

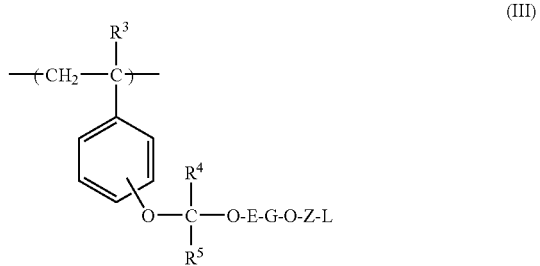

(III)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, Z represents a single bond, an alkylende group or a carbonyl group and L represents a phenyl group which is substituted with two C1-C6 alkoxy groups at 3- and 4-position and may be further substituted with at least one C1-C6 alkoxy group, a naphthyl group which may be substituted with at least one C1-C6 alkoxy group, an anthryl group which may be substituted with at least one C1-C6 alkoxy group, or a phenanthryl group which may be substituted with at least one C1-C6 alkoxy group, and (B') at least one acid generator;

<8> The chemically amplified positive resist composition according to <7>, wherein the polymerization unit represented by the formula (II) is a polymerization unit represented by the formula (IIa):

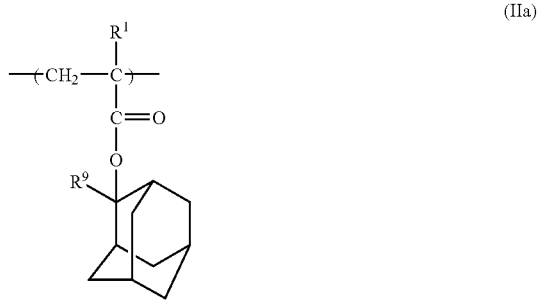

(IIa)

wherein $R^1$ represents a hydrogen atom or a methyl group and $R^9$ represents a C1-C8 alkyl group;

<9> The chemically amplified positive resist composition according to <7> or <8>, wherein p is 1 and q is 0 in the formula (I);

<10> The chemically amplified positive resist composition according to <7>, <8> or <9>, wherein at least one acid generator comprises diazomethane compound having a sulfonyl group;

<11> The chemically amplified positive resist composition according to any one of <7> to <10>, wherein the amount ratio of the resin (A1) and the resin (A2) is 5/95 to 50/50;

<12> The chemically amplified positive resist composition according to any one of <7> to <11>, wherein the chemically amplified positive resist composition further comprises a basic compound;

<13> A compound represented by the formula (V):

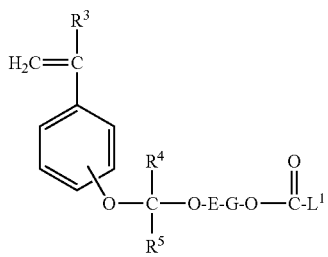

(V)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, and L' represents an anthryl group which may be substituted with at least one C1-C6 alkoxy group, or a phenanthryl group which may be substituted with at least one C1-C6 alkoxy group;

<14> A polymer comprising a polymerization unit represented by the formula (Va):

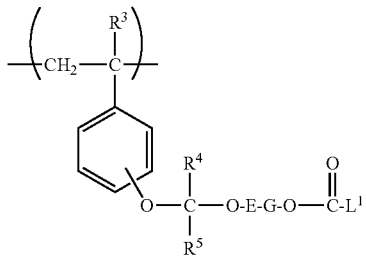

(Va)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, and L' represents an anthryl group which may be substituted with at least one C1-C6 alkoxy group, or a phenanthryl group which may be substituted with at least one C1-C6 alkoxy group.

DESCRIPTION OF PREFERRED EMBODIMENTS

The present chemically amplified positive resist composition (hereinafter, simply referred to as COMPOSITION 1) comprises (A) a resin which comprises (i) a polymerization unit represented by the formula (I), (ii) at least one polymerization unit selected from a group consisting of a polymerization unit represented by the formula (II), and a polymerization unit represented by the formula (IV), and (iii) a polymerization unit represented by the formula (III), and (B) at least one acid generator.

Hereinafter, the component (A) is simply referred to as the resin (A) and the component (B) is simply referred to as the acid generator (B). Hereinafter, a polymerization unit represented by the formula (I) is simply referred to as the polymerization unit (i). Hereinafter, at least one polymerization unit selected from a group consisting of a polymerization unit represented by the formula (II), and a polymerization unit represented by the formula (IV) is simply referred to as the polymerization unit (ii). Hereinafter, a polymerization unit represented by the formula (III) is simply referred to as the polymerization unit (iii).

In the formula (I), $R^7$ represents a hydrogen atom or a C1-C4 alkyl group, and $R^8$ represents a C1-C4 alkyl group.

Examples of the C1-C4 alkyl group include a methyl group, an ethyl group, an n-propyl group, an isopropyl group, an n-butyl group and a tert-butyl group. As $R^7$, a hydrogen atom or a methyl group is preferable and a hydrogen atom is more preferable.

In the formula (I), p represents an integer of 1 to 3, and p is preferably 1. In the formula (I), q represents an integer of 0 to 2, and q is preferably 0 or 1 and q is more preferably 0. When q is 1 or 2, $R^8$s may be the same or different.

The polymerization unit represented by the formula (I) is usually derived from a monomer represented by the formula (I-1):

(I-1)

wherein $R^7$, $R^8$, p and q are the same as defined above.

Preferable examples of the monomer represented by the formula (I-1) include a hydroxystyrene and more preferable examples thereof include p-hydroxystyrene.

In the formula (II), $R^1$ represents a hydrogen atom or a C1-C4 alkyl group, $R^2$ represents a C1-C8 alkyl group and ring X represents an alicyclic hydrocarbon group.

Examples oh the C1-C4 alkyl group include a methyl group, an ethyl group, an n-propyl group, an isopropyl group, an n-butyl group and a tert-butyl group. As $R^1$, a hydrogen atom or a methyl group is preferable. Examples of the C1-C8 alkyl group include a methyl group, an ethyl group, an n-propyl group, an isopropyl group, an n-butyl group, a tert-butyl group, an n-hexyl group and an n-octyl group. As $R^2$, a methyl group, an ethyl group, an n-propyl group and an isopropyl group are preferable and an ethyl group is more preferable.

Examples of the C1-C8 alkyl group include a methyl, ethyl, n-propyl, isopropyl, n-butyl, tert-butyl, n-pentyl, n-hexyl, cyclohexyl, n-octyl group, and a C1-C4 alkyl group is preferable, and ethyl and isopropyl group are preferable.

The alicyclic hydrocarbon group may be a monocyclic aliphatic hydrocarbon group or a polycyclic aliphatic hydrocarbon group. Preferable examples thereof include a cyclopentyl, cyclohexyl, adamantly and norbornyl group, and adamantly group is more preferable.

Preferable examples of the polymerization unit represented by the formula (II) include the following polymerization unit represented by the formula (IIa):

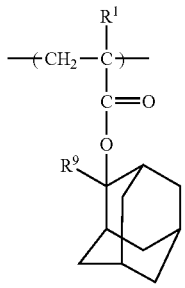

(IIa)

wherein $R^1$ represents a hydrogen atom or a C1-C4 alkyl group and $R^9$ represents a C1-C8 alkyl group.

The polymerization unit represented by the formula (II) is usually derived from a monomer represented by the formula (II-1):

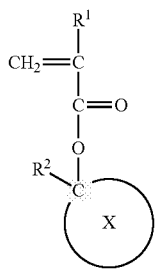

(II-1)

wherein $R^1$, $R^2$ and ring X are the same as defined above.

The polymerization unit represented by the formula (IIa) is usually derived from a monomer represented by the formula (IIa-1):

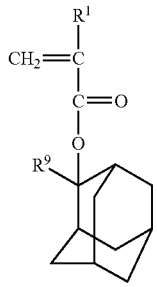

(IIa-1)

wherein $R^1$ and $R^9$ are the same as defined above.

Preferable examples of the monomer represented by the formula (IIa-1) include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-n-butyl-2-adamantyl acrylate, and 2-n-butyl-2-adamantyl methacrylate, and 2-ethyl-2-adamantyl acrylate and 2-ethyl-2-adamantyl methacrylate are more preferable.

In the formula (IV), $R^3$ represents a hydrogen atom or a C1-C4 alkyl group, $R^4$ and $R^5$ independently represents a hydrogen atom or a C1-C4 alkyl group, $R^{10}$ represents a C1-C6 alkyl group or a C5-C7 cycloalkyl group, and $R^4$ and $R^{10}$ or $R^5$ and $R^{10}$ may be bonded to form a trimethylene group or a tetramethylene group.

Examples of the C1-C4 alkyl group include a methyl group, an ethyl group, an n-propyl group, an isopropyl group, an n-butyl group and a tert-butyl group. As $R^3$, a hydrogen atom or a methyl group is preferable. As $R^4$, a hydrogen atom or a methyl group is preferable. As $R^5$, a hydrogen atom or a methyl group is preferable.

Examples of the C1-C6 alkyl group include a methyl group, an ethyl group, an n-propyl group, an isopropyl group, an n-butyl group, a tert-butyl group, an n-pentyl group and an n-hexyl group. Examples of the C5-C7 cycloalkyl group include a cyclopentyl group, a cyclohexyl group and a cycloheptyl group. As $R^{10}$, an ethyl group is preferable.

The polymerization unit represented by the formula (IV) can be derived from a monomer represented by the formula (IV-1):

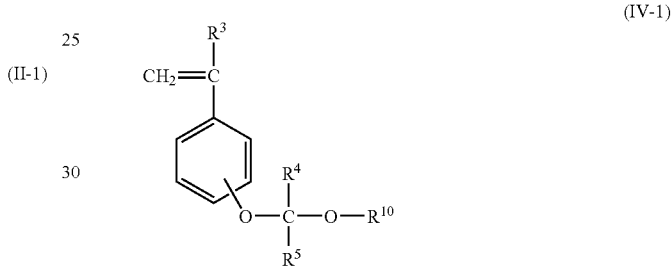

(IV-1)

wherein $R^3$, $R^4$, $R^5$ and $R^{10}$ are the same as defined above.

Examples of the monomer represented by the formula (IV-1) include p-(1-cyclohexyoxyethoxy)styrene and p-(1-ethoxyethyl)styrene.

Alternatively, a resin having the polymerization unit represented by the formula (IV) can be produced by a reaction of a resin having the polymerization unit represented by the formula (I-2):

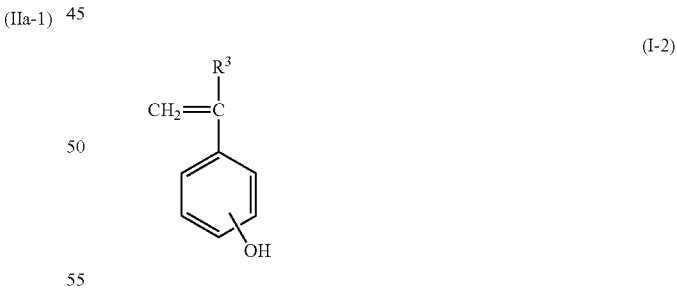

(I-2)

wherein $R^3$ is the same as defined above, and an alkoxyalkene compound. For example, a resin having the polymerization unit represented by the formula (IV) wherein $R^3$ is a hydrogen atom, $R^4$ is a methyl group, $R^5$ is a hydrogen atom and $R^{10}$ is an ethyl group, can be produced by a reaction of a resin having the polymerization unit represented by the formula (I-2) wherein $R^3$ is a hydrogen atom, and ethoxyethylene.

A resin having the polymerization unit represented by the formula (IV) wherein $R^3$ is a hydrogen atom, $R^4$ is a methyl group, $R^5$ is a hydrogen atom and $R^{10}$ is a cyclohexyl group, can be produced by a reaction of a resin having the polymerization unit represented by the formula (I-2) wherein $R^3$ is a hydrogen atom, and cyclohexyloxyethylene.

The polymerization unit represented by the formula (II) is preferable as the polymerization unit (ii).

In the formula (III), $R^3$, $R^4$ and $R^5$ are the same meanings as defined above. E represents a divalent hydrocarbon group. Examples of the divalent hydrocarbon group include a C1-C8 alkylene group which may have at least one cycloalkylene group such as a methylene group, an ethylene group, a trimethylene group, a tetramethylene group, a cyclohexane-1,4-dimethylene group and a cyclohexane-1,4-diethylene group.

G represents a single bond or a carbonyl group, and G is preferably a single bond.

Z represents a single bond, an alkylene group or a carbonyl group. Examples of the alkylene group include a C1-C8 alkylene group such as a methylene group, an ethylene group, a trimethylene group, a tetramethylene group, a pentamethylene group, a hexamethylene group and an octamethylene group. Z is preferably the carbonyl group.

L represents a phenyl group which is substituted with two C1-C6 alkoxy groups at 3- and 4-position and may be further substituted with at least one C1-C6 alkoxy group, a naphthyl group which may be substituted with at least one C1-C6 alkoxy group, an anthryl group which may be substituted with at least one C1-C6 alkoxy group, or a phenanthryl group which may be substituted with at least one C1-C6 alkoxy group.

Examples of the C1-C6 alkoxy group include a methoxy group, an ethyoxy group, an n-propoxy group, an isopropoxy group, an n-butoxy group, an isobutoxy group, an n-pentyloxy group and an n-hexyloxy group. Examples of the phenyl group which is substituted with two C1-C6 alkoxy groups at 3- and 4-position and may be further substituted with at least one C1-C6 alkoxy group include a 3,4-dimethyoxyphenyl group and a 3,4-diethoxyphenyl group. Examples of the naphthyl group which may be substituted with at least one C1-C6 alkoxy group include a 1-naphthyl group and 2-naphthyl group. Examples of the anthryl group which may be substituted with at least one C1-C6 alkoxy group include a 1-anthryl group, 2-anthryl group and 9-anthryl group. Examples of the phenanthryl group which may be substituted with at least one C1-C6 alkoxy group include a 1-phenanthryl group, a 2-phenanthryl group, a 3-phenanthryl group and a 9-phenanthryl group.

L is preferably an anthryl group which may be substituted with at least one C1-C6 alkoxy group, or a phenanthryl group which may be substituted with at least one C1-C6 alkoxy group, and more preferably an anthryl group which may be substituted with at least one C1-C6 alkoxy group.

The polymerization unit represented by the formula (III) is usually derived from a monomer represented by the formula (III-1):

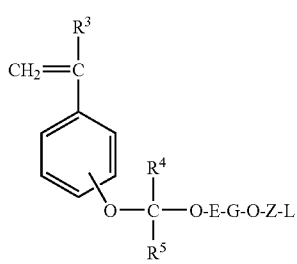

(III-1)

wherein $R^3$, $R^4$ and $R^5$ are the same as defined above.

Preferable examples of the monomer represented by the formula (III-1) include a compound represented by the formula (V):

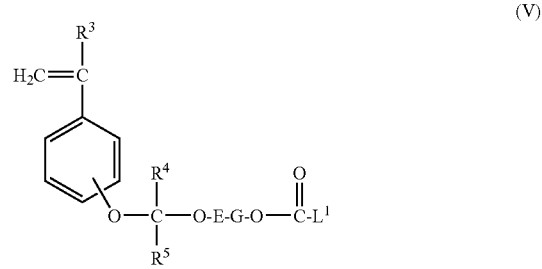

(V)

wherein $R^3$, $R^4$, $R^5$, E and G are the same as defined above, and L' represents an anthryl group which may be substituted with at least one C1-C6 alkoxy group, or a phenanthryl group which may be substituted with at least one C1-C6 alkoxy group.

For example, a resin having the polymerization unit represented by the formula (III) wherein $R^3$ is a hydrogen atom, $R^4$ is a methyl group and $R^5$ is a hydrogen atom, can be produced by a reaction of a resin having the polymerization unit represented by the formula (I-2):

(I-2)

wherein $R^3$ is a hydrogen atom, and an alkene compound represented by the following formula:

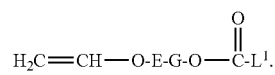

A compound represented by the formula (V) is a novel compound. A polymer comprising a polymerization unit represented by the formula (Va):

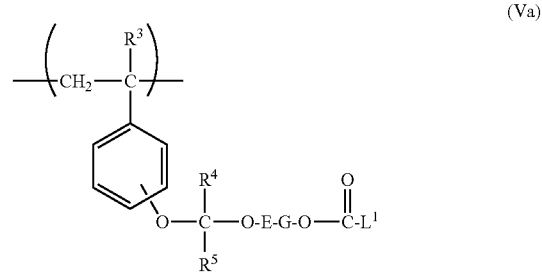

(Va)

wherein $R^3$, $R^4$, $R^5$, E, G and L' are the same meanings as defined above, is a novel polymer.

The content of the polymerization unit (i) is usually in the range of 20 to 99.8% by mole based on all polymerization units of the resin (A). The content of the polymerization unit (ii) is usually in the range of 0.1 to 50% by mole based on all polymerization units of the resin (A). The content of the polymerization unit (iii) is usually in the range of 0.1 to 30% by mole based on all polymerization units of the resin (A).

The resin (A) is usually produced by a polymerization of the corresponding monomers. A resin (A)can be also produced by polymerizing a monomer represented by the formula (I-3):

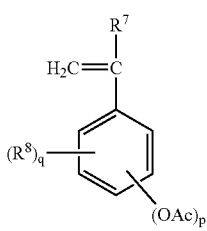

wherein $R^7$, $R^8$, p and q are the same as defined above, and Ac represents an acetyl group, at least one monomer selected from a group consisting of the monomer represented by the formula (II-1) and the monomer represented by the formula (IV-1), and the monomer represented by the formula (III-1) followed by hydrolyzing of the resin obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); a hydroperoxide such as tert-butyl hydroperoxide and benzoyl peroxide; an oxidation-reduction initiator such as hydrogenperoxide/ferrous salt and benzoyl peroxide/dimethylaniline; and an alkyl metal compound such as butyl lithium and triethylaluminum. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on molar amount of all monomers.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained. Examples thereof include a hydrocarbon solvent such as toluene; an ether solvent such as 1,4-dioxane and tetrahydrofuran; a ketone solvent such as methyl isobutyl ketone; an alcohol solvent such as methyl alcohol, ethyl alcohol, isopropyl alcohol tert-butyl alcohol; a cyclic ester solvent such as γ-butyrolactone; a glycol ether ester ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers.

After competition of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The resin (A) may have other polymerization unit or units.

Next, the acid generator (B) will be illustrated.

COMPOSITION 1 may contain an acid generator or two or more acid generators. COMPOSITION 1 preferable contains two or more acid generators.

The acid generator generates an acid by irradiation to itself or the composition containing the same, and the acid generated catalytically acts against the resin (A), and the resin (A) becomes soluble in an aqueous alkali solution.

The acid generator can be selected from various compounds generating the acid by irradiation with radiation on the acid generator itself or COMPOSITION 1.

As the acid generator, at least one selected from an onium salt, a halogenated alkyltriazine compound, a diazomethane compound having a sulfonyl group, a sulfonate compound and an imide compound having a sulfonyloxy group, is preferable. The onium salt, the diazomethane compound having a sulfonyl group and a mixture thereof are more preferable and a mixture of the onium salt and the diazomethane compound having a sulfonyl group is more preferable.

Examples of the onium salt include the salts represented by the formula (VIII):

$$A^{+-}O_3S-R^{23} \qquad (VIII)$$

wherein $R^{23}$ represents a linear or branched chain perfluoroalkyl group, or an aryl group which may be substituted, and $A^+$ represents an organic counter cation.

Examples of the linear or branched chain perfluoroalkyl group include a trifluoromethyl group, a pentafluoroethyl group, a heptafluoropropyl group, a nonafluorobutyl group and a perfluorooctyl group. The linear or branched chain C1-C8 perfluoroalkyl group is preferable.

Examples of the aryl group include a C6-C20 aryl group such as a phenyl group, a naphthyl group and an anthryl group. Examples of the substituent of the aryl group include a C1-C20 alkyl group, a C1-C20 alkoxy group and a halogen atom.

Examples of the C1-C20 alkyl group include a methyl group, an ethyl group, an n-propyl group, an isopropyl group, an n-butyl group, a tert-butyl group, an n-pentyl group, an n-hexyl group, an n-octyl group, an n-decyl group, an n-dodecyl group and an n-hexadecyl group.

Examples of the C1-C20 alkoxy group include a methoxy group, an ethoxy group, an n-propoxy group, an isopropoxy group, an n-butoxy group, a tert-butoxy group, an n-pentyloxy group, an n-hexyloxy group, an isopentyloxy group, an n-decyloxy group, an n-dodecyloxy group and an n-hexadecyloxy group.

Examples of the halogen atom include a fluorine, chlorine, bromine and iodine atom.

As $R^{23}$, the linear or branched chain C1-C8 perfluoroalkyl group and the phenyl group which may be substituted with at least one group selected from a C1-C20 alkyl group and a halogen atom are preferable.

Examples of the anion part of the salt represented by the formula (VIII) include the followings:

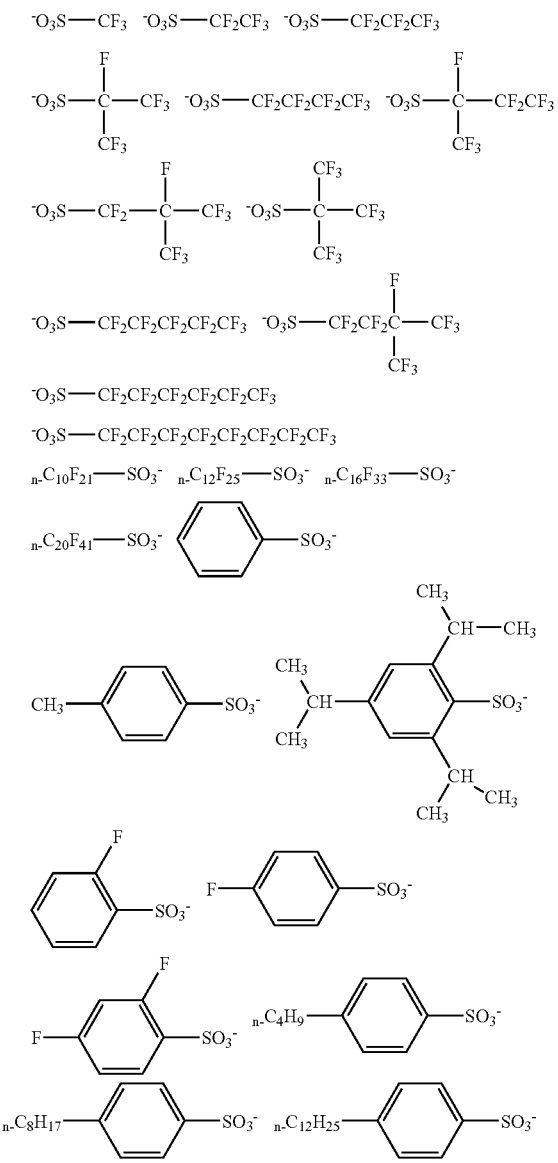

Examples of the organic counter cation include the following cations represented by the formulae (VIIIa), (VIIIb), (VIIc) and (VIIId):

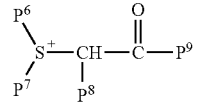

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (VIIIb):

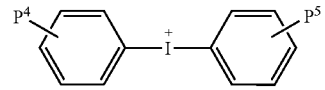

wherein $P^4$ and $P^5$ each independently represent a hydrogen atom, a hydroxyl group, a C1-C12 alkyl group or a C1-C12 alkoxy group, a cation represented by the formula (VIIIc):

(VIIIc)

$$\begin{array}{c} P^6 \\ | \\ S^+ - CH - C - P^9 \\ | \quad\quad | \quad \| \\ P^7 \quad P^8 \quad O \end{array}$$

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ bond to form a divalent acyclic hydrocarbon group which forms a 2-oxocycloalkyl group together with the adjacent —CHCO—, and at least one —$CH_2$— in the divalent acyclic hydrocarbon group may be substituted with —CO—, —O— or —S—, and a cation represented by the formula (VIIId):

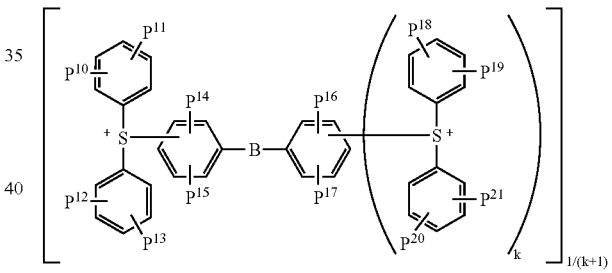

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

Examples of the C1-C12 alkoxy group in the formula (VIIIa) include a methoxy group, an ethoxy group, an n-propoxy group, an isopropoxy group, an n-butoxy group, an isobutoxy group, a sec-butoxy group, a tert-butoxy group, an n-pentyloxy group, an n-hexyloxy group, an n-octyloxy group and a 2-ethylhexyloxy group. Examples of the C3-C12 cyclic hydrocarbon group in the formula (VIIIa) include a cyclopentyl group, a cyclohexyl group, a 1-adamantyl group, a 2-adamantyl group, a phenyl group, a 2-methylphenyl group, a 4-methylphenyl group, a 1-naphthyl group and a 2-naphthyl group.

Examples of the C1-C30 alkyl group which may be substituted with at least one selected from the hydroxyl group, the C3-C12 cyclic hydrocarbon group and the C1-C12 alkoxy group in the formula (VIIIa) include a methyl group, an ethyl group, an n-propyl group, an isopropyl group, an n-butyl group, an isobutyl group, a sec-butyl group, a tert-butyl group, an n-pentyl group, an n-hexyl group, an n-octyl group, a 2-ethylhexyl group and a benzyl group.

Examples of the C3-C30 cyclic hydrocarbon group which may be substituted with at least one selected from the hydroxyl group and the C1-C12 alkoxy group in the formula (VIIIa) include a cyclopentyl group, a cyclohexyl group, a 1-adamantyl group, a 2-adamantyl group, a bicyclohexyl group, a phenyl group, a 2-methylphenyl group, a 4-methylphenyl group, a 4-ethylphenyl group, a 4-isopropylphenyl group, a 4-tert-butylphenyl group, a 2,4-dimethylphenyl group, a 2,4,6-trimethylphenyl group, a 4-n-hexylphenyl group, a 4-n-octylphenyl group, a 1-naphthyl group, a 2-naphthyl group, a fluorenyl group, a 4-phenylphenyl group, a 4-hydroxyphenyl group, a 4-methoxyphenyl group, a 4-tert-butoxyphenyl group, a 4-n-hexyloxyphen-yl group.

Examples of the C1-C12 alkyl group in the formulae (VIIIb), (VIIIc) and (VIIId) include a methyl group, an ethyl group, an n-propyl group, an isopropyl group, an n-butyl group, an isobutylgroup, a sec-butyl group, a tert-butyl group, an n-pentyl group, an n-hexyl group, an n-octyl group and a 2-ethylhexyl group. Examples of the C1-C12 alkoxy group in the formulae (VIIIb) and (VIIId) include the same groups as mentioned in the above formula (IIa).

Examples of the C3-C12 cycloalkyl group in the formula (VIIIc) include a cyclopropyl group, a cyclobutyl group, a cyclopentyl group, a cyclohexyl group, a cycloheptyl group, a cyclooctyl group and a cyclodecyl group. Examples of the C3-C12 divalent acyclic hydrocarbon group formed by bonding $P^6$ and $P^7$ include a trimethylene group, a tetramethylene group, a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the aromatic group in the formula (VIIIc) include a phenyl group, a tolyl group, a xylyl group and a naphthyl group. Examples of the divalent acyclic hydrocarbon group formed by bonding $P^8$ and $P^9$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (VIIIa) or (VIIIc) is preferable and the cation represented by the formula (VIIIa) is more preferable.

As the counter cation represented by $A^+$, cations represented by the following formulae (VIIIe), (VIIIf) and (VIIIg):

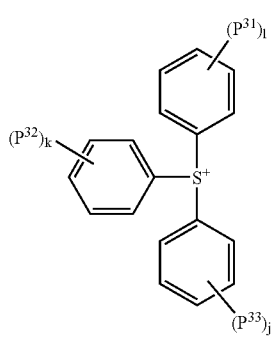

(VIIIe)

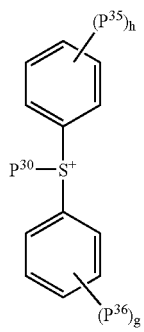

(VIIIf)

(VIIIg)

wherein $P^{28}$, $P^{29}$ and $P^{30}$ each independently represent a C1-C20 alkyl group or a C3-C30 cyclic hydrocarbon group except a phenyl group, and at least one hydrogen atom in the C1-C20 alkyl group may be substituted with a hydroxyl group, a C1-C12 alkoxy group or a C3-C12 cyclic hydrocarbon group and at least one hydrogen atom in the C3-C30 cyclic hydrocarbon group may be substituted with a hydroxyl group, a C1-C12 alkyl group or a C1-C12 alkoxy group, and $P^{31}$, $P^{32}$, $P^{33}$, $P^{34}$, $P^{35}$ and $P^{36}$ each independently represent a hydroxyl group, a C1-C12 alkyl group, a C1-C12 alkoxy group or a C3-C12 cyclic hydrocarbon group, and l, k, j, i, h and g each independently represent an integer of 0 to 5, are also preferable.

Examples of the C1-C20 alkyl group include a methyl group, an ethyl group, an n-propyl group, an isopropyl group, an n-butyl group, a tert-butyl group, an n-hexyl group, an n-octyl group, an n-decyl group and an n-icosyl group.

Examples of the C1-C12 alkoxy group and the C3-C30 cyclic hydrocarbon group include the same groups as mentioned above.

As the counter cation represented by $A^+$, a cation represented by the formula (VIIIh):

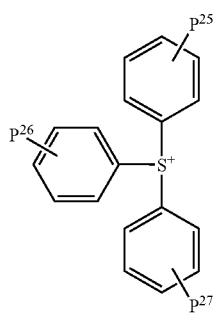

(VIIIh)

wherein $P^{25}$, $P^{26}$ and $P^{27}$ each independently represent a hydrogen atom, a hydroxyl group, a C1-C12 alkyl group or a C1-C12 alkoxy group, is more preferable, and a cation represented by the formula (VIIIi):

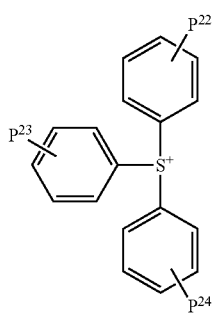
(VIIIi)
wherein $P^{22}$, $P^{23}$ and $P^{24}$ each independently represent a hydrogen atom or a C1-C4 alkyl group, is especially preferable.
Examples of the alkyl group and the alkoxy group include the same groups as mentioned above.
Examples of the cation represented by the formula (VIIIa) include the followings.
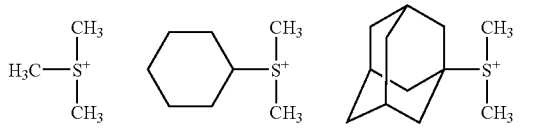
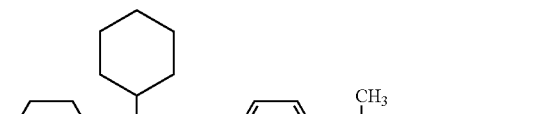
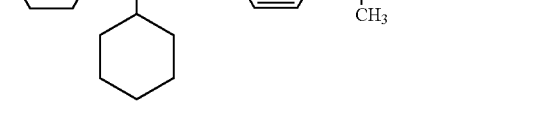
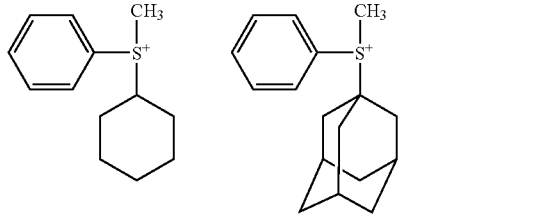
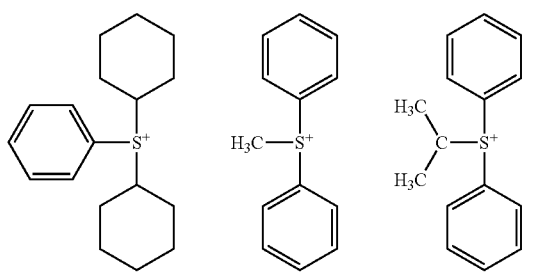
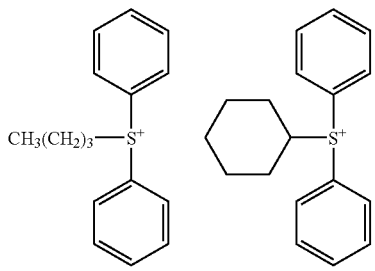
-continued
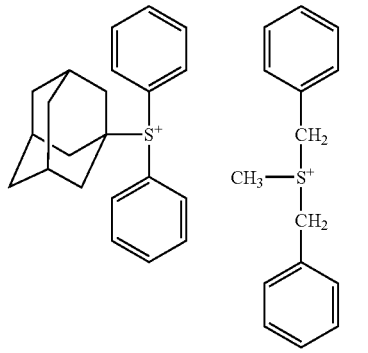
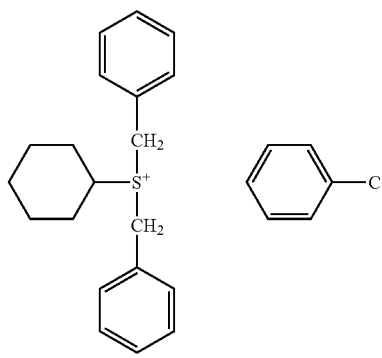
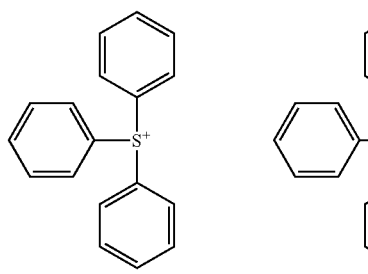
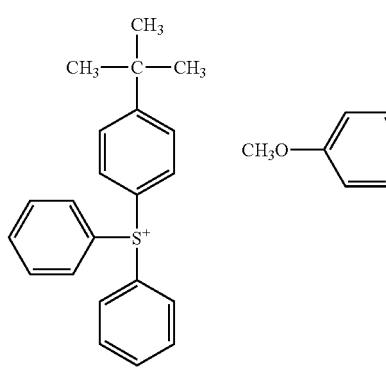

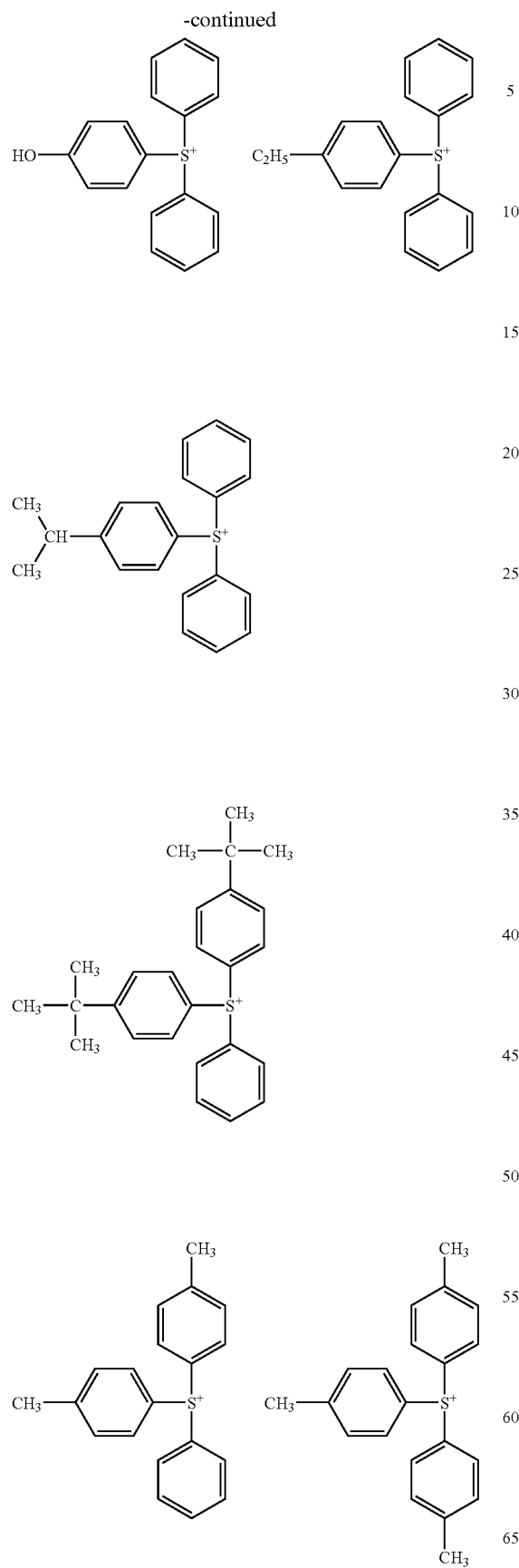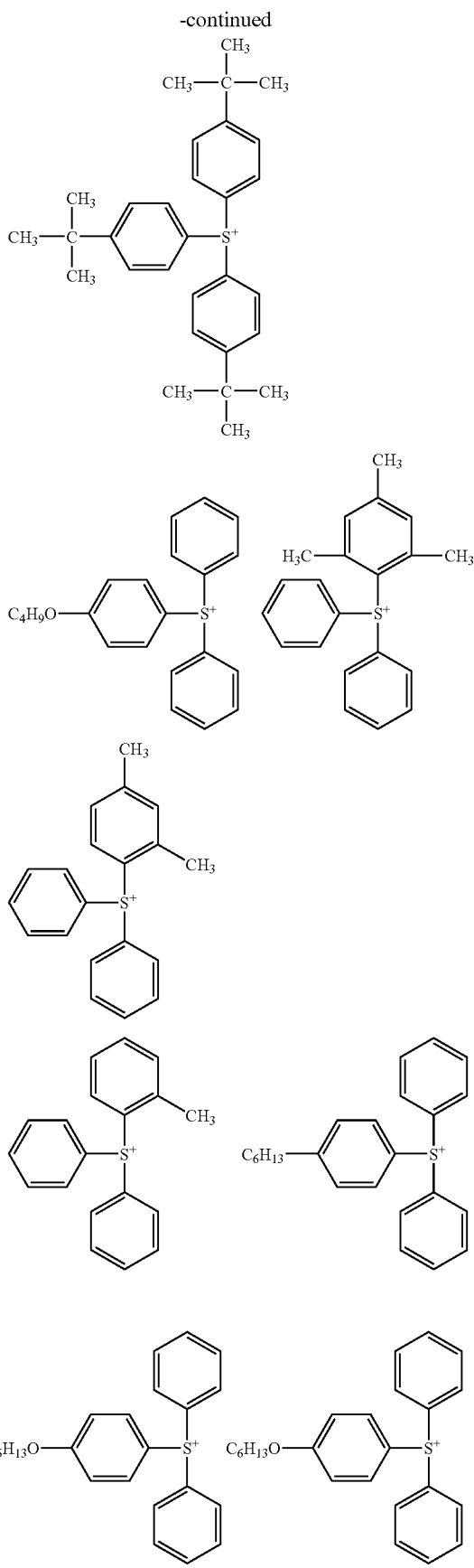

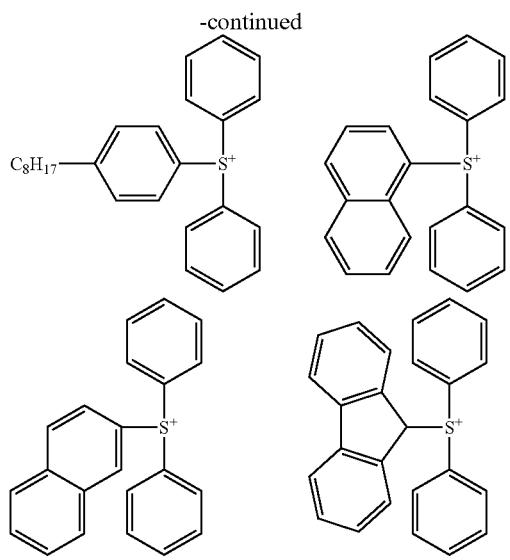
Examples of the cation represented by the formula (VIIIb) include the followings.
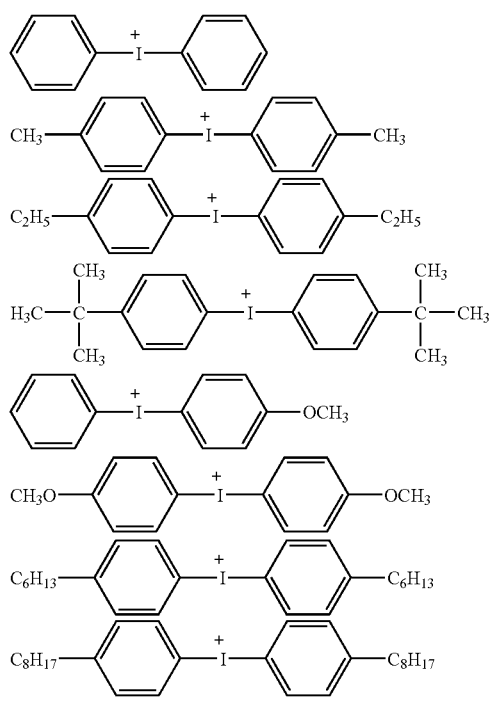
Examples of the cation represented by the formula (VIIIc) include the followings.
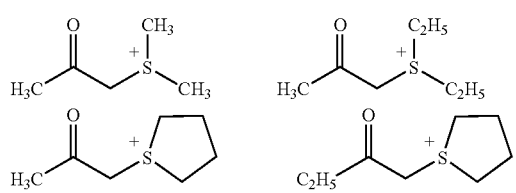
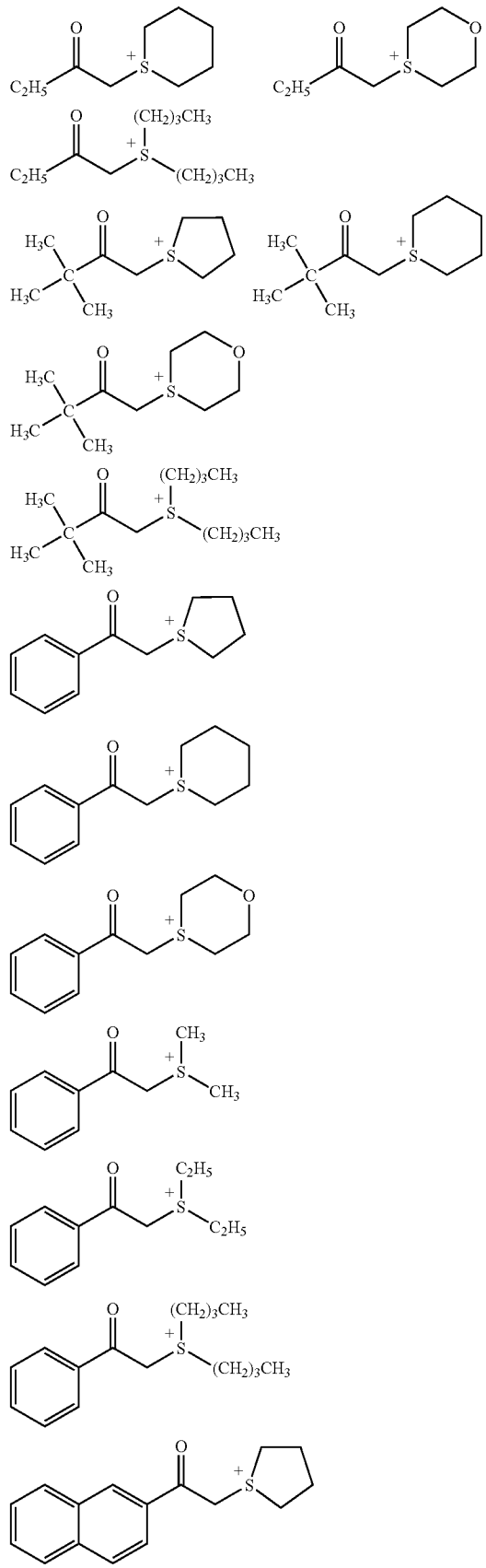

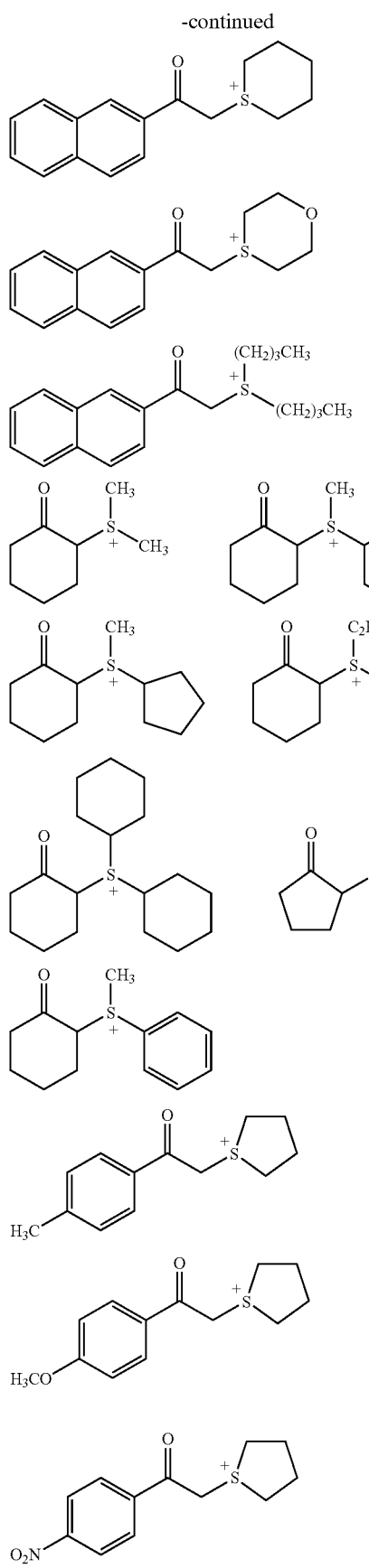
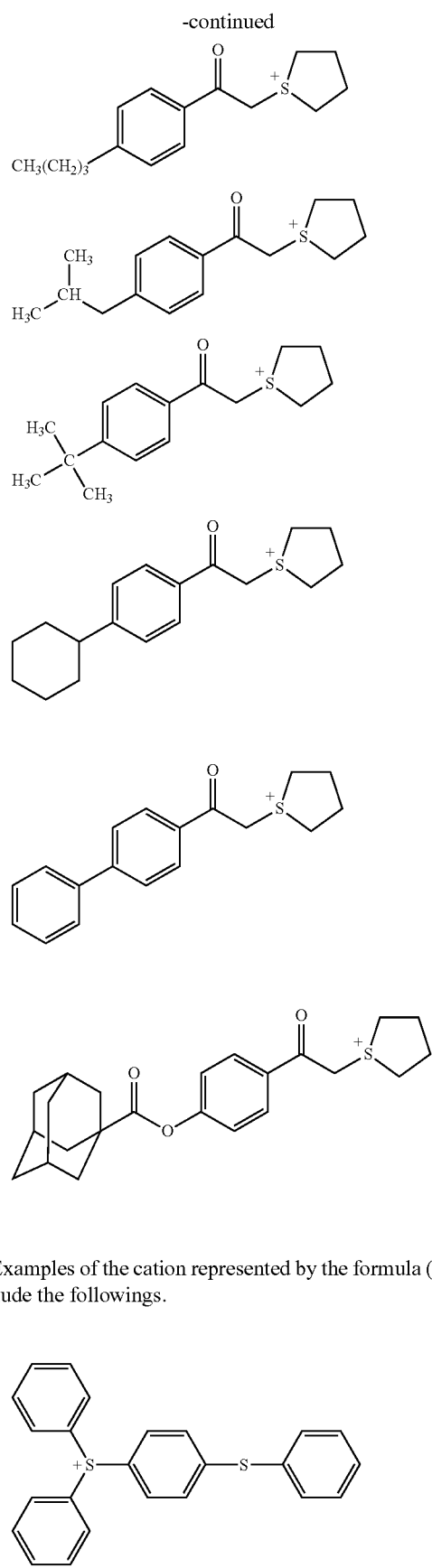
Examples of the cation represented by the formula (VIIId) include the followings.
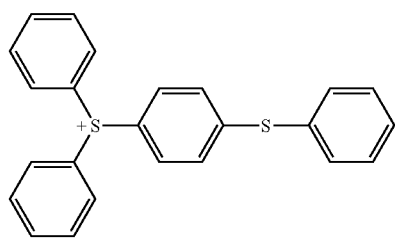

-continued
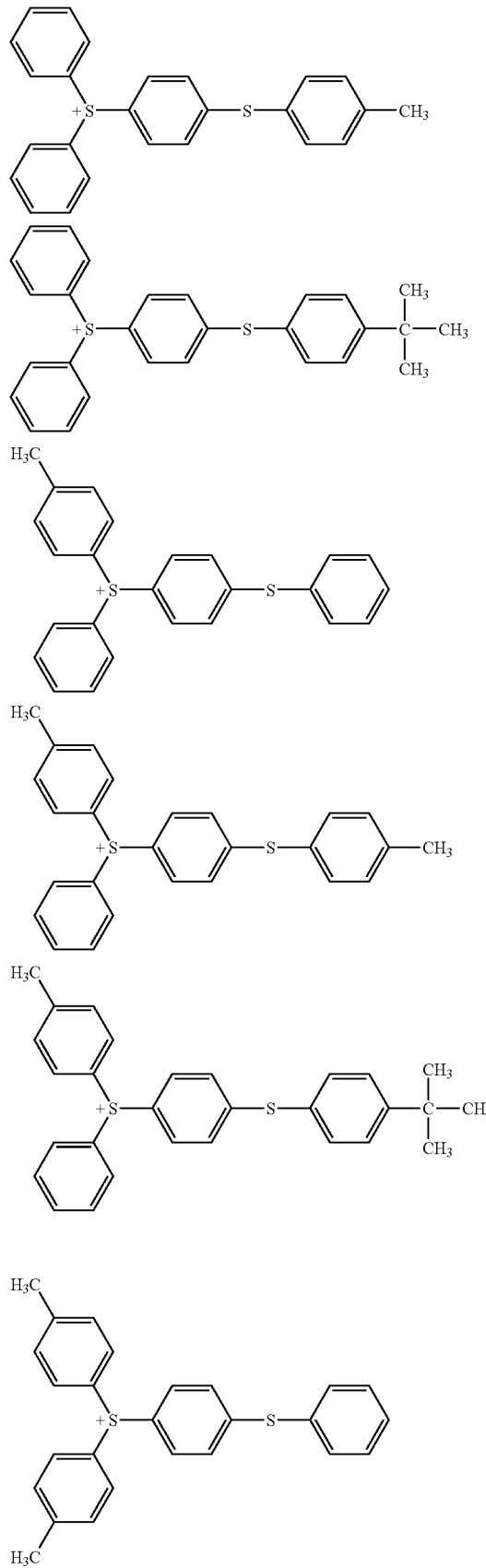
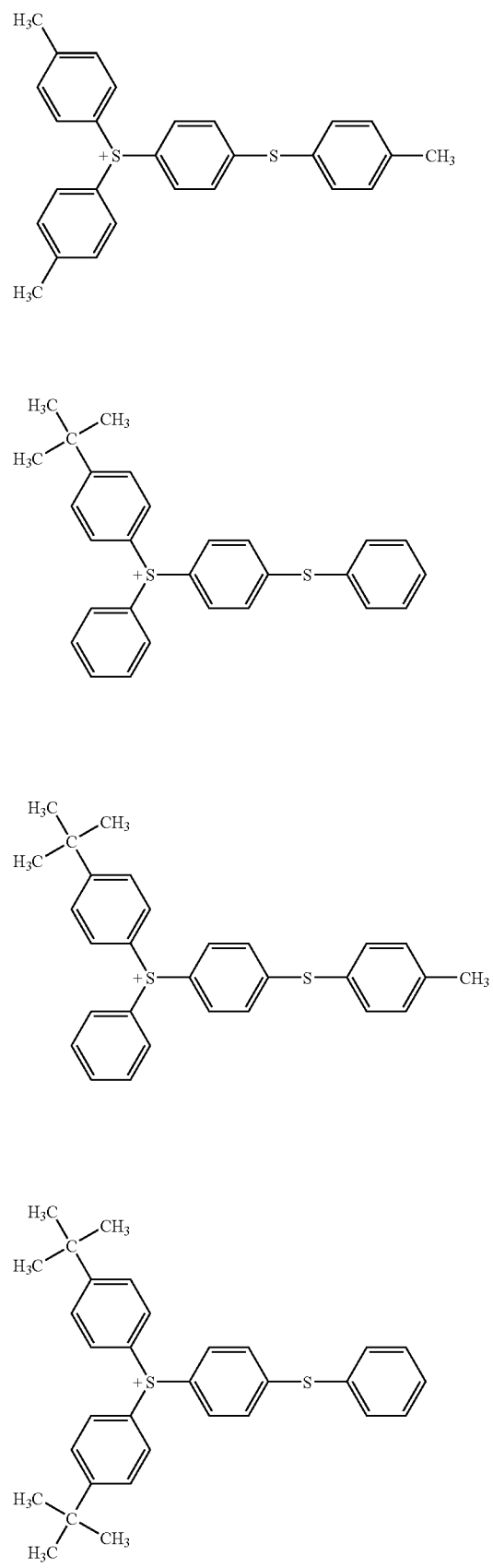

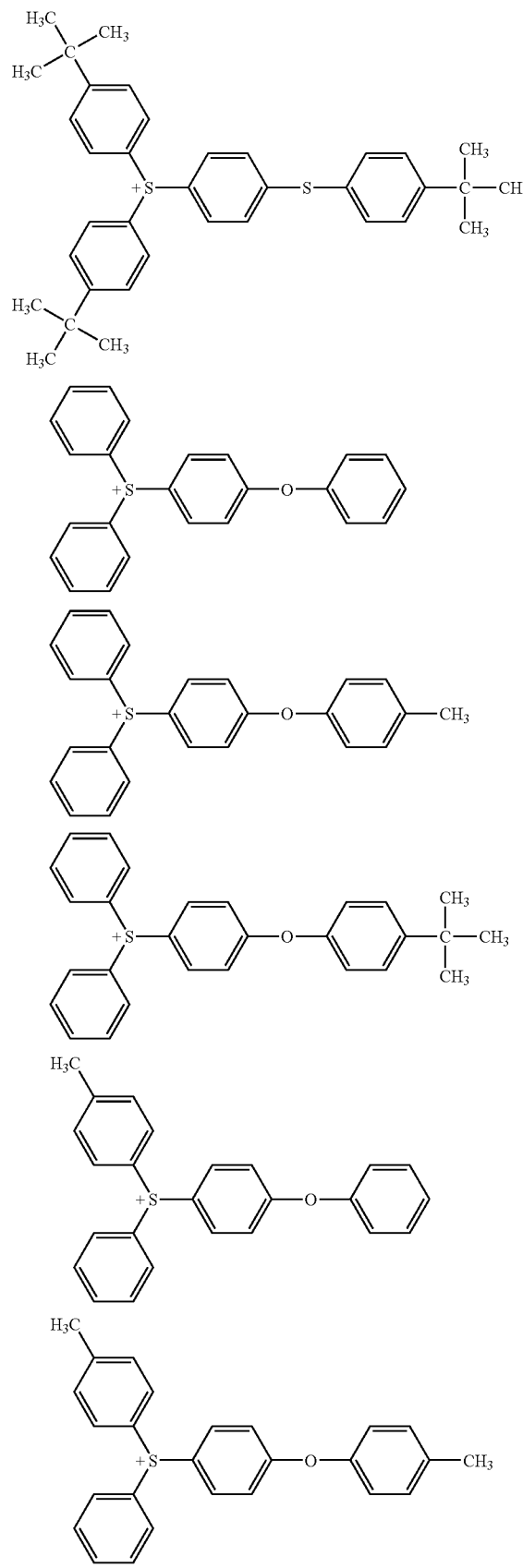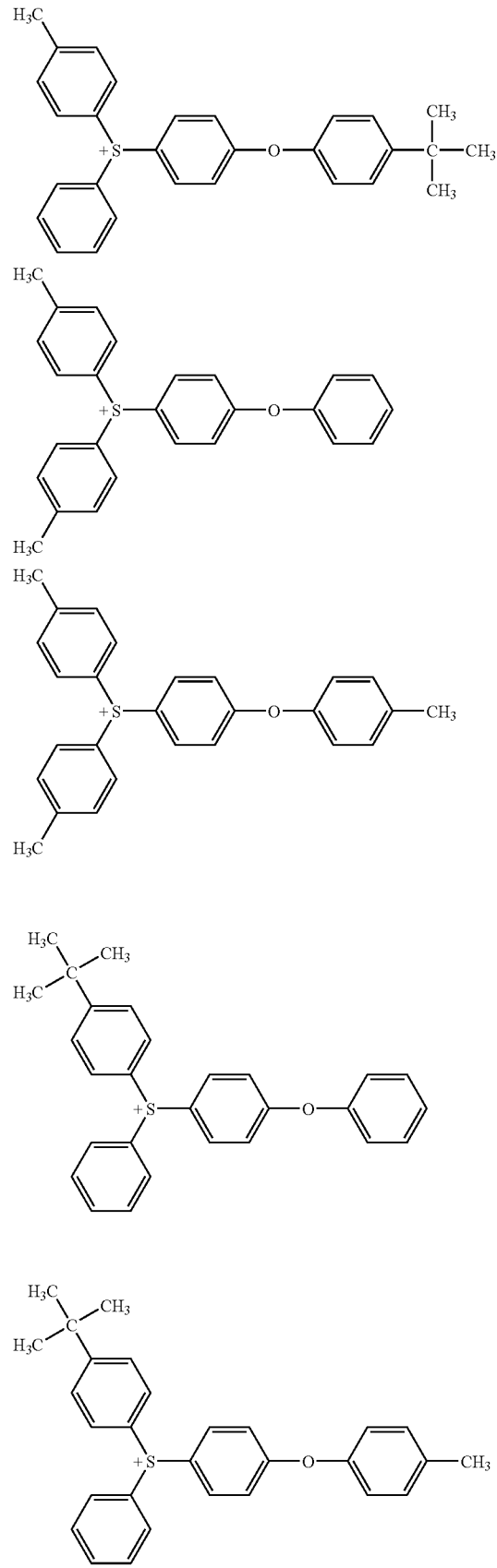

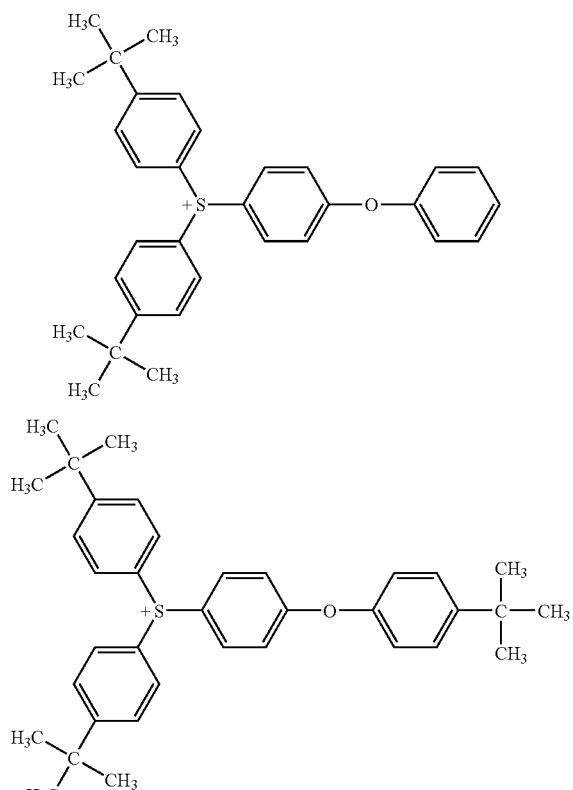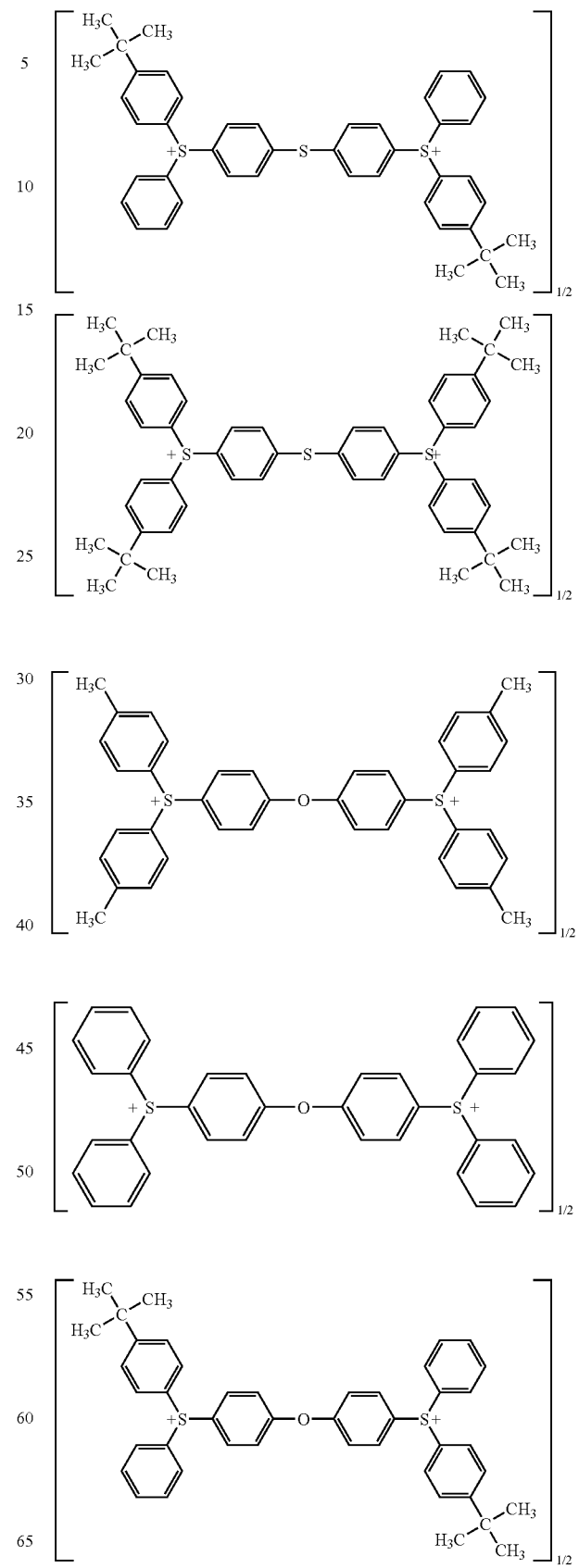

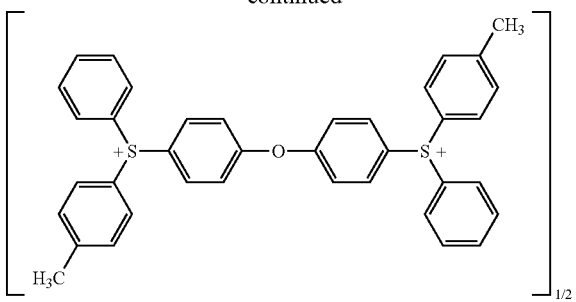

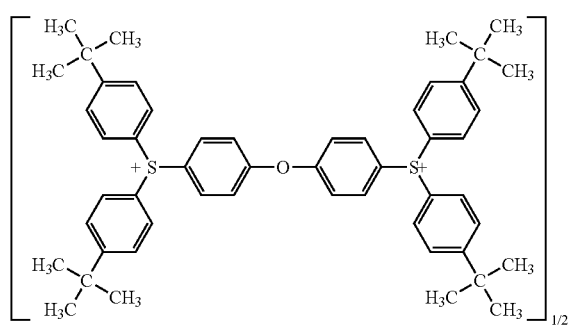

Examples of the halogenated alkyltriazine compound include 2-methyl-4,6-bis(trichloromethyl)-1,3,5-triazine, 2,4,6-tris(trichloromethyl)-1,3,5-triazine, 2-phenyl-4,6-bis(trichloromethyl)-1,3,5-triazine, 2-(4-chlorophenyl)-4,6-bis(trichloromethyl)-1,3,5-triazine, 2-(4-methoxyphenyl)-4,6-bis(trichloromethyl)-1,3,5-triazine, 2-(4-methoxy-1-naphthyl)-4,6-bis(trichloromethyl)-1,3,5-triazine, 2-(benzo[d][1,3]dioxoran-5-yl)-4,6-bis(trichloromethyl)-1,3,5-triazine, 2-(4-methoxystyryl)-4,6-bis(trichloromethyl)-1,3,5-triazine, 2-(3,4,5-trimethoxystyryl)-4,6-bis(trichloromethyl)-1,3,5-triazine, 2-(3,4-dimethoxystyryl)-4,6-bis(trichloromethyl)-1,3,5-triazine, 2-(2,4-methoxystyryl)-4,6-bis(trichloromethyl)-1,3,5-triazine, 2-(2-methoxystyryl)-4,6-bis(trichloromethyl)-1,3,5-triazine, 2-(4-butoxystyryl)-4,6-bis(trichloromethyl)-1,3,5-triazine and 2-(4-pentyloxystyryl)-4,6-bis(trichloromethyl)-1,3,5-triazine.

Examples of the sulfonate compound include 1-benzoyl-1-phenylmethyl p-toluenesulfonate (generally called "benzoin tosylate"), 2-benzoyl-2-hydroxy-2-phenylethyl p-toluenesulfonate (generally called "α-methylolbenzoin tosylate"), 1,2,3-benzene-tri-yl tris(methanesulfonate), 2,6-dinitrobenzyl p-toluenesulfonate, 2-nitrobenzyl p-toluenesulfonate and 4-nitrobenzyl p-toluenesulfonate.

Examples of the imide compound having a sulfonyloxy group include N-(phenylsulfonyloxy)succinimide, N-(trifluoromethylsulfonyloxy)succinimide, N-(trifluoromethylsulfonyloxy)phthalimide, N-(trifluoromethylsulfonyloxy)-5-norbornene-2,3-dicarboxyimide, N-(trifluoromethylsulfonyloxy)naphthalimide and N-(10-camphorsulfonyloxy)naphthalimide.

Examples of the diazomethane compound having a sulfonyl group include a compound represented by the formula (IX):

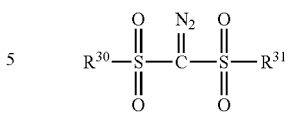

wherein $R^{30}$ and $R^{31}$ independently represents a C3-C8 linear, branched chain or cyclic alkyl group or an aryl group which may be substituted.

Examples of the C3-C8 linear, branched chain or cyclic alkyl group include an n-propyl group, an isopropyl group, an n-butyl group, an isobutyl group, a tert-butyl group, an n-pentyl group, an n-hexyl group, an n-octyl group, a cyclopentyl group and a cyclohexyl group.

Examples of the substitutent of the aryl group include a halogen atom such as a fluorine atom, a chlorine atom and a bromine atom.

Examples of the aryl group which may be substituted include a phenyl group, a 4-chlorophenyl group, a p-tolyl group, a 2,4-xylyl group, a 4-isopropylphenyl group, a 4-tert-butylphenyl group, a naphthyl group and an anthryl group.

Examples of the compound represented by the formula (IX) include bis(n-propylsulfonyl)diazomethane, bis(isopropylsulfonyl)diazomethane, bis(n-butylsulfonyl)diazomethane, bis(tert-butylsulfonyl)diazomethane, bis(cyclopentylsulfonyl)diazomethane, bis(cyclohexylsulfonyl)diazomethane, bis(phenylsulfonyl)diazomethane, bis(4-chlorophenylsulfonyl)diazomethane, bis(p-tolylsulfonyl)diazomethane, bis(4-tert-butylphenylsulfonyl)diazomethane, bis(2,4-xylylsulfonyl)diazomethane, bis(4-isopropylphenylsulfonyl)diazomethane, bis(naphthylsulfonyl)diazomethane, and bis(anthrylsulfonyl)diazomethane.

Among them, bis(cyclohexylsulfonyl)diazomethane and bis(tert-butylsulfonyl)diazomethane are preferable.

As the onium salt, a salt represented by the formula (VII):

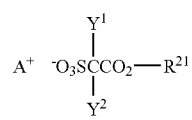

wherein $R^{21}$ represents a C1-C30 hydrocarbon group which may be substituted, and at least one —$CH_2$— in the hydrocarbon group may be substituted by —CO— or —O—, $Y^1$ and $Y^2$ each independently represent a fluorine atom or a C1-C6 perfluoroalkyl group, and $A^+$ is the same as defined above, is exemplified.

$R^{21}$ preferably represents a group represented by the formula:

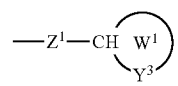

wherein $Z^1$ represents a single bond or —$(CH_2)_f$—, f represents an integer of 1 to 4, $Y^3$ represents —CO— or —CH(OH)—; ring $W^1$ represents a C3-C30 monocyclic or polycyclic hydrocarbon group in which a hydrogen atom is substituted with a hydroxyl group at $Y^3$ position when $Y^3$ is —CH(OH)— or in which two hydrogen atoms are substituted with =O at $Y^3$ position when $Y^3$ is —CO—, and at least one hydrogen atom in the C3-C30 monocyclic or polycyclic hydrocarbon group may be substituted with a C1-C6 alkyl group, a C1-C6 alkoxy group, a C1-C4 perfluoroalkyl group, a C1-C6 hydroxyalkyl group, a hydroxyl group or a cyano group.

The C1-C30 hydrocarbon group may be a linear or branched chain hydrocarbon group. The C1-C30 hydrocarbon group may have a monocyclic or polycyclic structure, and may have an aromatic group or groups. The C1-C30 hydrocarbon group may have a carbon-carbon double bond or bonds.

It is preferred that the C1-C30 hydrocarbon group has at least one cyclic structure, and it is more preferred that the C1-C30 hydrocarbon group has a cyclic structure. Examples of the cyclic structure include a cyclopropane, cyclohexane, cyclooctane, norbornane, adamantane, cyclohexene, benzene, naphthalene, anthracene, phenanthrene and fluorene structure.

Examples of the substituent include a C1-C6 alkyl group, a C1-C6 alkoxy group, a C1-C4 perfluoroalkyl group, a C1-C6 hydroxyalkyl group, a hydroxyl group or a cyano group, and the hydroxyl group is preferable as the substituent.

Examples of the C1-C6 alkyl group include a methyl group, an ethyl group, an n-propyl group, an isopropyl group, an n-butyl group, an isobutyl group, a sec-butyl group, a tert-butyl group, an n-pentyl group and an n-hezyl group. Examples of the C1-C6 alkoxy group include a methoxy group, an ethoxy group, an n-propoxy group, an isopropoxy group, an n-butoxy group, an isobutoxy group, a seq-butoxy group, a tert-butoxy group, an n-pentyloxy group and an n-hexyloxy group. Examples of the C1-C4 perfluoroalkyl group include a trifluoromethyl group, a pentafluoroethyl group, a heptafluoropropyl group and a nonafluorobutyl group. Examples of the C1-C6 hydroxyalkyl group include a hydroxymethyl group, a 2-hydroxyethyl group, a 3-hydroxypropyl group, a 4-hydroxybutyl group and a 6-hydroxyhexyl group.

$Y^1$ and $Y^2$ each independently represent a fluorine atom or a C1-C6 perfluoroalkyl group. Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and the trifluoromethyl group is preferable.

It is preferable that $Y^1$ and $Y^2$ each independently represent the fluorine atom or the trifluoromethyl group, and it is more preferable that $Y^1$ and $Y^2$ represent the fluorine atoms.

Specific examples of the ring $W^1$ include a 2-oxocyclopentyl group, a 2-oxocyclohexyl group, a 3-oxocyclopentyl group, a 3-oxocyclohexyl group, a 4-oxocyclohexyl group, a 2-hydroxycyclopentyl group, a 2-hydroxycyclohexyl group, a 3-hydroxycyclopentyl group, a 3-hydroxycyclohexyl group, a 4-hydroxycyclohexyl group, a 4-oxo-2-adamantyl group, a 3-hydroxy-1-adamantyl group, a 4-hydroxy-1-adamantyl group, a 5-oxonorbornan-2-yl group, a 1,7,7-trimethyl-2-oxonorbornan-2-yl group, a 3,6,6-trimethyl-2-oxobicyclo[3.1.1]heptan-3-yl group, a 2-hydroxy-norbornan-3-yl group, a 1,7,7-trimethyl-2-hydroxynorbornan-3-yl group, a 3,6,6-trimethyl-2-hydroxybicyclo[3.1.1]heptan-3-yl group, In the formulae above, straight line with an open end shows a bond which is extended from an adjacent group.

As the ring $W^1$, the adamantane ring is preferable. The group represented by the following formulae (l) and (m):

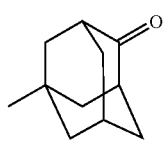

(1)

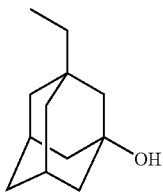
(m)

is preferable as $R^{21}$. In the above formulae (l) and (m), straight line with an open end shows a bond which is extended from an adjacent group.

It is preferable that COMPOSITION 1 contains the resin (A) in an amount of about 80 to 99.9% by weight and the acid generator (B) in an amount of 0.1 to 20% by weight on the total amount of the resin (A) and the acid generator (B).

COMPOSITION 1 may contain the other resin. Examples of the other resin include a resin having a polymerization unit represented by the formula (I) and a resin having polymerization units represented by the formulae (I) and (II). When COMPOSITION 1 contains a resin having a polymerization unit represented by the formula (I) or a resin having polymerization units represented by the formula (I) and (II) in addition to the resin (A), the content of the resin having a polymerization unit represented by the formula (I) or the resin having polymerization units represented by the formula (I) and (II) is usually 0 to 90% by weight based on all resin components.

Another chemically amplified positive resist composition of the present invention (hereinafter, simply referred to as COMPOSITION 2) comprises (A1) a resin which comprises (iv) a polymerization unit represented by the formula (I) and (v) at least one polymerization unit selected from a group consisting of a polymerization unit represented by the formula (II) and a polymerization unit represented by the formula (IV), (A2) a resin which comprises (vi) the polymerization unit represented by the formula (I) and (vii) a polymerization unit represented by the formula (III), and (B') at least one acid generator.

Hereinafter, the component (A1) is simply referred to as the resin (A1), the component (A2) is simply referred to as the resin (A2) and the component (B') is simply referred to as the acid generator (B'). Hereinafter, in the resin (A1), a polymerization unit represented by the formula (I) is simply referred to as the polymerization unit (iv), at least one polymerization unit selected from a group consisting of a polymerization unit represented by the formula (II) and a polymerization unit represented by the formula (IV) is simply referred to as the polymerization unit (v). Hereinafter, in the resin (A2), the polymerization unit represented by the formula (I) is simply referred to as the polymerization unit (vi) and a polymerization unit represented by the formula (III) is simply referred to as the polymerization unit (vii).

The resins (A1) and (A2) can be produced by polymerization of the corresponding monomers according to the same method as the method for producing the resin (A) described above.

It is preferable that COMPOSITION 2 contains the resins (A1) and (A2) in an amount of about 80 to 99.9% by weight and the acid generator (B') in an amount of 0.1 to 20% by weight on the total amount of the resin (A1), the resin (A2) and the acid generator (B').

The ratio of the resin (A1) and the resin (A2) is usually 1/999 to 999/1.

The content of the polymerization unit (iv) is usually in the range of 30 to 90% by mole based on all polymerization units of the resin (A1). The content of the polymerization unit (v) is usually in the range of 70 to 10% by mole based on all polymerization units of the resin (A1).

The content of the polymerization unit (vi) is usually in the range of 40 to 99.9% by mole based on all polymerization units of the resin (A2), and the content of the polymerization unit (vii) is usually in the range of 60 to 0.01% by mole based on all polymerization units of the resin (A2).

COMPOSITION 2 may contain an acid generator or two or more acid generators. COMPOSITION 2 preferable contains two or more acid generators.

The acid generator generates an acid by irradiation to itself or the composition containing the same, and the acid generated catalytically acts against the resins (A1) and (A2), and the resins (A1) and (A2) become soluble in an aqueous alkali solution.

The acid generator can be selected from various compounds generating the acid by irradiation with radiation on the acid generator itself or COMPOSITION 2.

As the acid generator, at least one selected from an onium salt, a halogenated alkyltriazine compound, a diazomethane compound having a sulfonyl group, a sulfonate compound and an imide compound having a sulfonyloxy group, is preferable. The onium salt, the diazomethane compound having a sulfonyl group and a mixture thereof are more preferable and a mixture of the onium salt and the diazomethane compound having a sulfonyl group is more preferable.

COMPOSITION 2 may contain the other resin. Examples of the other resin include a resin having a polymerization unit represented by the formula (I). When COMPOSITION 2 contains a resin having a polymerization unit represented by the formula (I) in addition to the resin (A1) and the resin (A2), the content of the resin having a polymerization unit represented by the formula (I) is usually 0 to 90% by weight based on all resin components.

In COMPOSITION 1 and COMPOSITION 2, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

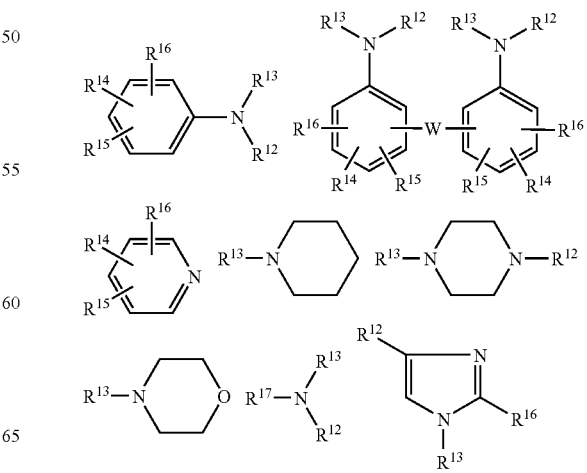

-continued

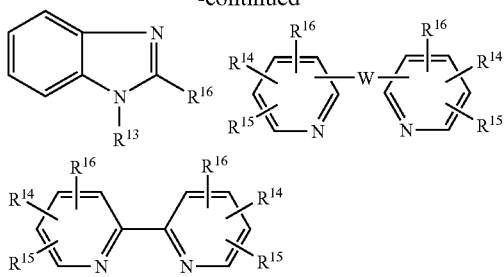

wherein $R^{12}$ and $R^{13}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{14}$ and $R^{15}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{14}$ and $R^{15}$ bond together with the carbon atoms to which they bond to form an aromatic ring, $R^{16}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{17}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

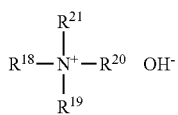

wherein $R^{18}$, $R^{19}$, $R^{20}$ and $R^{21}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{12}$, $R^{13}$, $R^{14}$, $R^{15}$, $R^{16}$, $R^{17}$, $R^{18}$, $R^{19}$, $R^{20}$ and $R^{21}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{12}$, $R^{13}$, $R^{14}$, $R^{15}$, $R^{16}$, $R^{17}$, $R^{18}$, $R^{19}$, $R^{20}$ and $R^{21}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The in $R^{12}$, $R^{13}$, $R^{14}$, $R^{15}$, $R^{17}$, $R^{18}$, $R^{19}$, $R^{20}$ and $R^{21}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{14}$, $R^{15}$ and $R^{16}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-dlyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.001 to 2% by weight of the basic compound based on the total amount of the resin component, the acid generator and the basic compound.

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted.

The weight-average molecular weight and degree of dispersion (the weight-average molecular weight of the resin obtained/the molar-average molecular weight of the resin obtained) of any resin in the following Examples is a value found by gel permeation chromatography using polystyrene as a standard reference material. The structures of obtained compounds were checked by NMR analysis.

Synthesis Example 1

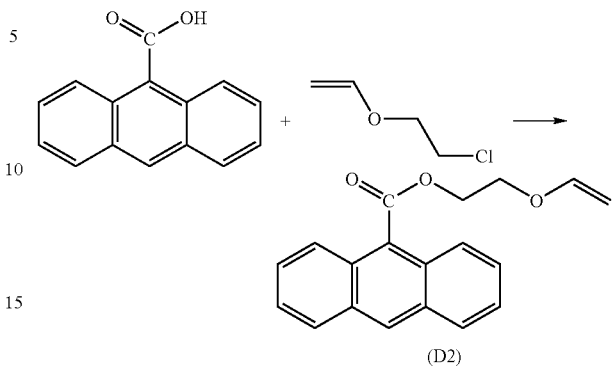

Five parts of 9-anthracene-9-carboxylic acid was dissolved in 35 parts of N,N-dimethylformamide. To the obtained solution, 3.1 parts of potassium carbonate and 0.9 part of potassium iodide were added and the resultant mixture was heated at 50° C. for 1 hour while stirring.

To the solution, 2.4 parts of chloroethyl vinyl ether was added dropwise over 1 hour at 50° C., and the resultant mixture was heated at 50° C. for 5.5 hour and further at 100° C. for 3.5 hour. The mixture was cooled below about 20° C. and 46.4 parts of ion-exchanged water was added to the mixture. The obtained mixture was extracted four times with 23.2 parts of ethyl acetate and the ethyl acetate layers obtained were mixed to obtain a solution and the solution was washed five times with 30 parts of ion-exchanged water. The solution was mixed with 0.8 part of active carbon and 4.0 parts of magnesium sulfate and the obtained mixture was stirred. The mixture was filtrated and the obtained filtrate was concentrated to obtain the yellow solid. The yellow solid was mixed with 18.1 parts of n-heptane and the mixture obtained was filtrated and the obtained solid was dried to obtain 5.2 parts of 2-vinyloxyethyl antracene-9-carboxylate in a form of yellow solid. The compound obtained is called as D2.

$^1$H-NMR (dimethylsulfoxide-$d_6$, internal standard: tetramethylsilane) δ (ppm) 4.04 (dd, 1H, J=1.8 Hz, 6.6 Hz), 4.08-4.11 (m, 2H), 4.30 (dd, 1H, J=1.8 Hz, 14.2 Hz), 4.80-4.83 (m, 2H), 6.61 (dd, 1H, J=6.8 Hz, 14.2 Hz), 7.54-7.65 (m, 4H), 8.02 (d, 2H, J=9.7 Hz), 8.17 (d, "H, J=9.7 Hz), 8.78 (s, 1H)

MS (ESI(+) Spectrum): [M+Na]$^+$ 315.1 ($C_{19}H_{36}NaO_3^+$= 315.10)

RESIN SYNTHESIS EXAMPLE 1

Into the flask, 22.3 g of a methyl isobutyl ketone solution of poly(p-hydroxyxtyrene) containing 7.5 parts of poly(p-hydroxyxtyrene) wherein the weight-average molecular weight of poly(p-hydroxytyrene) was about 15,200, and the degree of dispersion of poly(p-hydroxytyrene) was 1.20), 0.0012 part of p-toluenesulfonic acid monohydrate and 30.2 parts of methyl isobutyl ketone were charged. To the obtained solution, 9.4 parts of the compound D2 was added with 6 parts of methyl isobutyl ketone and the resultant mixture was stirred at 25° C. for 3.5 hours. The mixture was mixed with 18 parts of ion-exchanged water to separate. The obtained organic layer was washed four times with 18 parts of ion-exchanged water and concentrated. The obtained residue was mixed with 56 parts of propylene glycol monomethyl ether acetate and the obtained mixture was concentrated to obtain 58.8 parts of a propylene glycol monomethyl ether acetate solution containing a resin. The solid content of the solution obtained was measured by a method for measuring loss on heating. The solid content of the solution obtained was 35.4%.

The polymerization units of the resin obtained were following polymerization units (A) and (B).

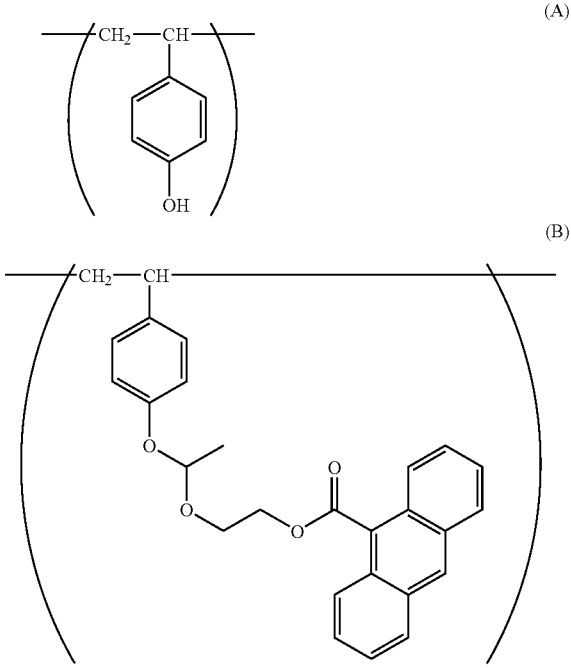

From the result of $^{13}$C-NMR analysis, the content of the polymerization unit (B) was 19.7%. The resin obtained is called as A1.

REIN SYNTHESIS EXAMPLE 2

Into a flask, 103.8 parts of 4-acetoxystyrene, 39.7 parts of 2-ethyl-2-adamantyl methacrylate and 265 parts of isopropanol were charged. The resultant mixture was heated to 75° C. under an atmosphere of nitrogen, and then, a solution prepared by mixing 22.11 parts of isopropanol and 11.05 parts of dimethyl-2,2'-azobis(2-methylpropionate) was added dropwise to the mixture. The resultant mixture was kept at 75° C. for about 0.3 hour and further refluxed for about 12 hours. The reaction mixture obtained was diluted with acetone and the obtained mixture was poured into a large amount of methanol. The resin precipitated was collected by filtration to obtain 250 parts of a resin. The resin obtained was contained methanol.

The polymerization units of the resin obtained were following polymerization units (A') and (C).

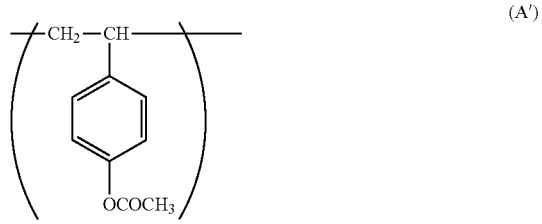

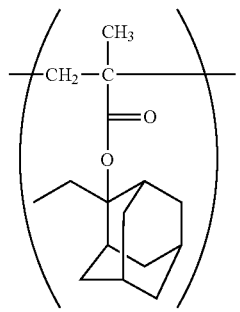

The ratio of the polymerization units (A') and (C) in the resin was 80/20.

Into a flask, 250 parts of the resin obtained above, 202 parts of methanol and 10.3 parts of 4-dimethylaminopyridine were charged and the resultant mixture was refluxed for 20 hours. The mixture obtained was cooled and then, was neutralized with 7.6 parts of glacial acetic acid. The mixture obtained was poured into a large amount of water and the resin precipitated was collected by filtration. The resin was dissolved with acetone and the solution obtained was poured into a large amount of water to precipitate a resin. This operation was repeated three times to obtain 95.9 parts of a resin. The polymerization units of the resin obtained were following polymerization units (A) and (C).

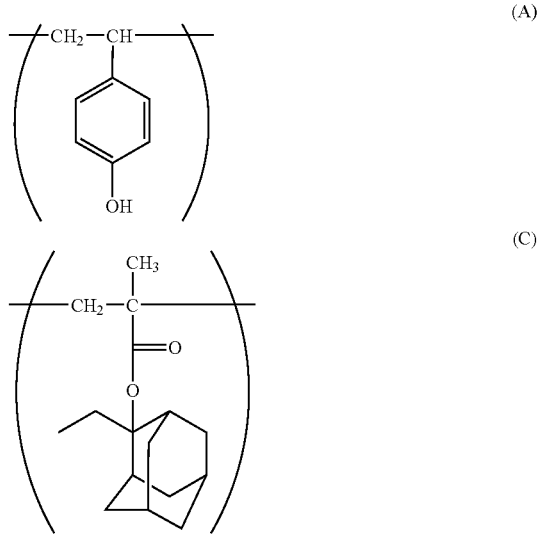

The resin obtained is called as A3.

The weight-average molecular weight of the resin A3 was about 8,600 and the degree of dispersion of the resin A3 was 1.65. The ratio of the polymerization units (A) and (C) in the resin A3 was about 80/20 by $^{13}$C-NMR analysis.

RESIN SYNTHESIS EXAMPLE 3

Twenty parts of the resin A3 obtained in Resin Synthesis Example 2 was dissolved with 120 parts of methyl isobutyl ketone and the resultant solution was concentrated to obtain 80 parts of a solution containing the resin A3. To the solution, 0.003 part of p-toluenesulfonic acid monohydrate and 57 parts of methyl isobutyl ketone were added. To the obtained solution, 5.9 parts of the compound D2 was added and the resultant mixture was stirred at 25° C. for 3 hours. The mixture was mixed with 36 parts of ion-exchanged water to separate. The obtained organic layer was washed four times with 36 parts of ion-exchanged water and concentrated. The obtained residue was mixed with 150 parts of propylene glycol monomethyl ether acetate and the obtained mixture was concentrated to obtain 64.9 parts of a propylene glycol monomethyl ether acetate solution containing a resin. The solid content of the solution obtained was measured by a method for measuring loss on heating. The solid content of the solution obtained was 39.6% by a result of measurement by a method for measuring loss on heating. The resin obtained is called as A2.

The polymerization units of the resin A2 were following polymerization units (A), (B) and (C).

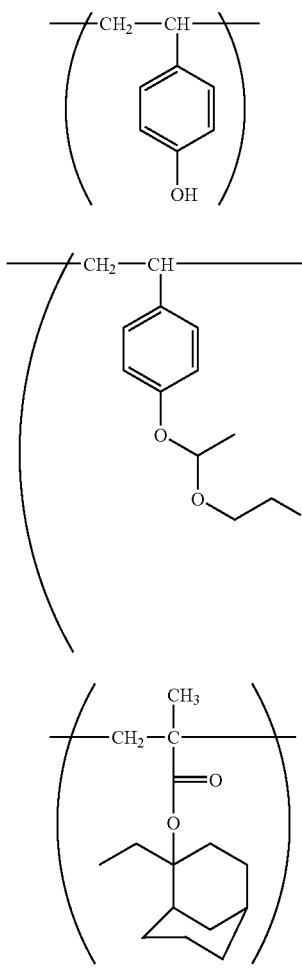

From the result of $^{13}$C-NMR analysis, the ratio of the polymerization units (A) and (B) in the resin A2 was 92.7/7.3 by $^{13}$C-NMR analysis.

RESIN SYNTHESIS EXAMPLE 4

Into a flask, 90.8 parts of 4-acetoxystyrene, 59.6 parts of 2-ethyl-2-adamantyl methacrylate and 279 parts of isopropanol were charged. The resultant mixture was heated to 75° C. under an atmosphere of nitrogen, and then, a solution prepared by mixing 22.11 parts of isopropanol and 11.05 parts of dimethyl-2,2'-azobis(2-methylpropionate) was added dropwise to the mixture. The resultant mixture was kept at 75° C. for about 0.3 hour and further refluxed for about 12 hours. The reaction mixture obtained was diluted with acetone and the obtained mixture was poured into a large amount of methanol. The resin precipitated was collected by filtration to obtain 250 parts of a resin. The resin obtained was contained methanol.

The polymerization units of the resin obtained were above-mentioned following polymerization units (A') and (C).

The ratio of the polymerization units (A') and (C) in the resin was 70/30.

Into a flask, 250 parts of the resin obtained above, 239 parts of methanol and 10.8 parts of 4-dimethylaminopyridine were charged and the resultant mixture was refluxed for 20 hours. The mixture obtained was cooled and then, was neutralized with 8 parts of glacial acetic acid. The mixture obtained was poured into a large amount of water and the resin precipitated was collected by filtration. The resin was dissolved with acetone and the solution obtained was poured into a large amount of water to precipitate a resin. This operation was repeated three times to obtain 102.8 parts of a resin. The polymerization units of the resin obtained were following polymerization units (A) and (C).

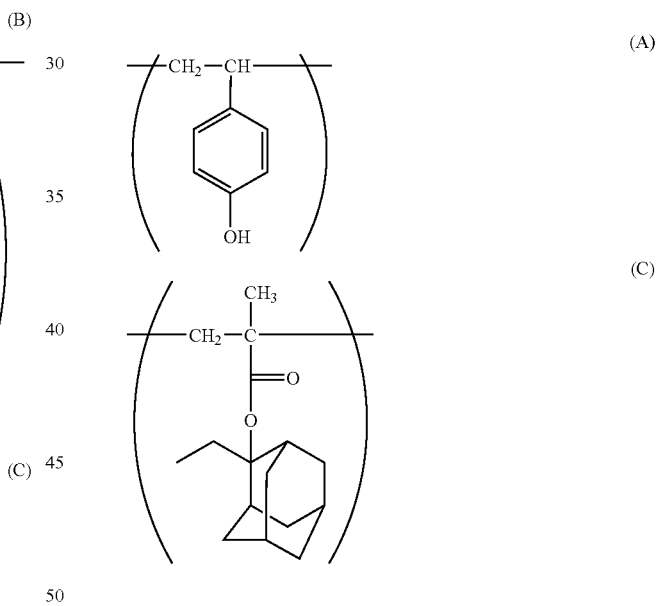

The resin obtained is called as A4.

The weight-average molecular weight of the resin A4 was about 8,200 and the degree of dispersion of the resin A4 was 1.68. The ratio of the polymerization units (A) and (C) in the resin A4 was about 70/30 by $^{13}$C-NMR analysis.

<Acid Generator>
Acid generator B1: triphenylsulfonium 2,4,6-triisopropybenzenesulfonate
Acid generator B2: bis(cyclohexylsulfonyl)diazomethane <Quencher>
Quencher C1: diisopropylaniline <Solvent>
Solvent S1: propylene glycol monomethyl ether acetate/propylene glycol monomethyl ether (weight ratio=8/2)

EXAMPLES 1 to 2 AND COMPARATIVE EXAMPLE 1

The following components were mixed to give a solution, and the solution was further filtrated through a fluorine resin filter having a pore diameter of 0.2 μm, to prepare resist liquid.

Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent (kind/amount (part)) |
|---|---|---|---|---|
| Ex. 1 | A1/15.2 A3/84.8 | B1/3.33 B2/6.67 | C1/0.44 | S1/1333 |
| Ex. 2 | A2/34.1 A3/65.9 | B1/3.33 B2/6.67 | C1/0.44 | S1/1333 |
| Comp. Ex. 1 | A3/50 A4/50 | B1/3.33 B2/3.33 | C1/0.44 | S1/1333 |

Each of the resist liquids prepared as above was spin-coated over the silicon wafer. After coating each of the resist liquids, the silicon wafers thus coated with the respective resist liquids were each prebaked on a proximity hotplate at a temperature of 90° C. for 60 seconds to form resist film of which thickness was 0.24 μm. Using a KrF excimer laser stepper ("NSR-2205EX12B" manufactured by Nikon Corporation, NA=0.55, σ=0.80), each wafer on which the respective resist film had been thus formed was exposed via several masks having different shapes and size.

After the exposure, each wafer was subjected to post-exposure baking on a hotplate at a temperature of 110° C. for 60 seconds and then to paddle development for 60 seconds with an aqueous solution of 2.38% tetramethylammonium hydroxide.

Each of a pattern developed on the substrate after the development was observed with a scanning electron microscope, and the results of which are shown in Table 2.

Effective Sensitivity (ES): It is expressed as the amount of exposure that the line and space pattern become 1:1 after exposure through 0.25 μm line and space pattern mask and development.

Resolution: It is expressed as the minimum size of space pattern which gave the space pattern split by the line pattern at the exposure amount of the effective sensitivity.

Profile: Each of a wall surface of pattern developed on the organic anti-reflective coating substrate after the development was observed with a scanning electron microscope. When the wall surface was a waved pattern, an amplitude of the wave pattern was high, and T-top was found, its evaluation was marked by "X", when the wall surface was flat or nearly flat pattern, its evaluation was marked by "○", and when the wall surface was a waved pattern and an amplitude of the waved pattern was low, its evaluation was marked by "Δ".

TABLE 2

| Ex. No. | Profile | Resolution (μm) |
|---|---|---|
| Ex. 1 | ○ | 0.20 |
| Ex. 2 | ○ | 0.20 |
| Comp. Ex. 1 | X | 0.22 |

Each of the resist liquids prepared as above was spin-coated over the several silicon wafers. After coating each of the resist liquids, the silicon wafers thus coated with the respective resist liquids were each prebaked on a proximity hotplate at a temperature of 90° C. for 60 seconds to form the several resist films of which thickness were 0.20 to 0.30 μm. Using a KrF excimer laser stepper ("NSR-2205EX12B" manufactured by Nikon Corporation, NA=0.55, σ=0.80), each wafer on which the respective resist film had been thus formed was exposed.

After the exposure, each wafer was subjected to post-exposure baking on a hotplate at a temperature of 110° C. for 60 seconds and then to paddle development for 60 seconds with an aqueous solution of 2.38% tetramethylammonium hydroxide.

Each of a pattern developed on the substrate after the development was observed with a scanning electron microscope.

The line and space patterns after exposure through 0.25 μm line and space pattern mask and development at the constant exposure amount were observed. The line widths of the patterns (CD) were measured and the differences between the maximum line width of the pattern and the minimum line width of the pattern (CD-SW) were calculated. The smaller the value of CD-SW was, the better the pattern was.

The results are shown in Table 3.

TABLE 3

| Ex. No. | CD-SW (nm) |
|---|---|
| Ex. 1 | 45 |
| Ex. 2 | 36 |
| Comp. Ex. 1 | 143 |

The present chemically amplified positive resist compositions give patterns having high resolution and good profile.

What is claimed is:

1. A compound represented by the formula (V):

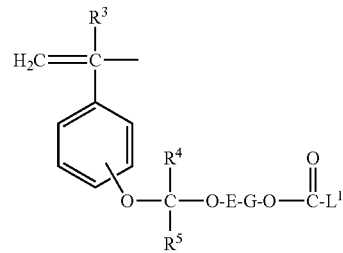

(V)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, and L' represents an anthryl group which may be substituted with at least one C1-C6 alkoxy group, or a phenanthryl group which may be substituted with at least one C1-C6 alkoxy group.

2. A polymer comprising a polymerization unit represented by the formula (Va):

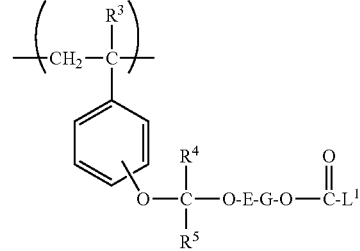

(Va)

wherein $R^3$ represents a hydrogen atom or a C1-C4 alkyl group, $R^4$ and $R^5$ independently represents a hydrogen atom or a C1-C4 alkyl group, E represents a divalent hydrocarbon group, G represents a single bond or a carbonyl group, and L' represents an anthryl group which may be substituted with at least one C1-C6 alkoxy group, or a phenanthryl group which may be substituted with at least one C1-C6 alkoxy group.

* * * * *